United States Patent
Goetz et al.

(10) Patent No.: US 8,890,681 B2
(45) Date of Patent: Nov. 18, 2014

(54) MANAGEMENT OF SESSION HISTORY DATA FOR IMPLANTABLE FLUID DELIVERY DEVICE

(75) Inventors: Steven M. Goetz, North Oaks, MN (US); Sarah B. Alme, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 880 days.

(21) Appl. No.: 12/730,751

(22) Filed: Mar. 24, 2010

(65) Prior Publication Data
US 2010/0265072 A1    Oct. 21, 2010

Related U.S. Application Data

(60) Provisional application No. 61/170,363, filed on Apr. 17, 2009.

(51) Int. Cl.
| | | |
|---|---|---|
| G08B 1/08 | (2006.01) | |
| G06F 19/00 | (2011.01) | |
| A61M 5/142 | (2006.01) | |
| A61M 5/14 | (2006.01) | |

(52) U.S. Cl.
CPC .... G06F 19/3468 (2013.01); *A61M 2205/3569* (2013.01); *A61M 2205/52* (2013.01); G06F 19/3487 (2013.01); *A61M 2005/1402* (2013.01); *A61M 5/14276* (2013.01); *A61M 2205/505* (2013.01); *A61M 2205/3523* (2013.01); *Y10S 128/903* (2013.01); *Y10S 128/13* (2013.01)
USPC .............. 340/539.12; 340/286.07; 128/903; 128/DIG. 13

(58) Field of Classification Search
USPC .............. 340/539.12, 539.29, 286.07, 573.1; 128/903, 920, 923, DIG. 13; 600/300, 600/301, 587; 607/60, 62, 67
See application file for complete search history.

(56) References Cited

U.S. PATENT DOCUMENTS 5,693,076 A * 12/1997 Kaemmerer .................... 607/59
5,722,999 A    3/1998 Snell
(Continued)

FOREIGN PATENT DOCUMENTS

| EP | 1 022 035 A1 | 7/2000 |
|---|---|---|
| EP | 1 681 069 A1 | 7/2006 |

(Continued)

OTHER PUBLICATIONS

Patent Application entitled, "Display of Supplemental Bolus in Relation to Programmed Dose," U.S. Appl. No. 12/691,513, filed Jan. 21, 2010.

(Continued)

*Primary Examiner* — Brent Swarthout
(74) *Attorney, Agent, or Firm* — Shumaker & Sieffert, P.A.

(57) ABSTRACT

This disclosure describes techniques for displaying representations of therapy session histories with a programmer device configured to program an implantable fluid delivery device. Information regarding the session histories may be stored in a memory of the fluid delivery device. An example programmer includes a user interface comprising a display to present a representation of a plurality of therapy sessions administered by an implantable fluid delivery device to a patient, and a processor that controls the user interface to present on the display the representation of the plurality of therapy sessions. The representation may include simultaneously displayed, temporally-ordered representations of the plurality of therapy sessions, such as a graph comprising a plurality of nodes, each node corresponding to one of the therapy sessions. Horizontal locations of the nodes may correspond to relative ending dates for the corresponding therapy session, and shapes of each node may represent infusion patterns.

45 Claims, 24 Drawing Sheets

(56) References Cited

U.S. PATENT DOCUMENTS

| | | | |
|---|---|---|---|
| 5,925,066 A * | 7/1999 | Kroll et al. | 607/3 |
| 6,007,493 A | 12/1999 | Ericksen et al. | |
| 6,442,433 B1 * | 8/2002 | Linberg | 607/60 |
| 6,675,044 B2 * | 1/2004 | Chen | 607/30 |
| 7,027,871 B2 | 4/2006 | Burnes et al. | |
| 7,047,065 B2 | 5/2006 | Kalgren et al. | |
| 7,072,725 B2 | 7/2006 | Bristol et al. | |
| 7,347,854 B2 | 3/2008 | Shelton et al. | |
| 7,366,570 B2 * | 4/2008 | Riff et al. | 607/27 |
| 2001/0012955 A1 * | 8/2001 | Goedeke et al. | 607/27 |
| 2001/0047194 A1 | 11/2001 | Thompson et al. | |
| 2002/0150872 A1 | 10/2002 | Glenn et al. | |
| 2002/0193679 A1 * | 12/2002 | Malave et al. | 600/407 |
| 2004/0088020 A1 | 5/2004 | Condie et al. | |
| 2004/0181204 A1 | 9/2004 | Jasperson et al. | |
| 2005/0043863 A1 * | 2/2005 | Ali et al. | 700/900 |
| 2005/0283210 A1 | 12/2005 | Blischak et al. | |
| 2006/0041222 A1 | 2/2006 | Dewing et al. | |
| 2006/0206066 A1 | 9/2006 | Ferek-Petric | |
| 2006/0272652 A1 | 12/2006 | Stocker et al. | |
| 2008/0033402 A1 | 2/2008 | Blomquist | |
| 2008/0177254 A1 | 7/2008 | Shelton et al. | |
| 2008/0286330 A1 * | 11/2008 | Shafer et al. | 424/423 |
| 2009/0093756 A1 * | 4/2009 | Minaie et al. | 604/67 |
| 2011/0253586 A1 * | 10/2011 | Metry et al. | 206/531 |
| 2011/0264071 A1 | 10/2011 | Braig et al. | |

FOREIGN PATENT DOCUMENTS

| | | |
|---|---|---|
| EP | 1845466 A2 | 10/2007 |
| WO | WO 03/099355 A2 | 12/2003 |
| WO | WO 2005/009514 A2 | 2/2005 |
| WO | WO 2005/107419 A2 | 11/2005 |
| WO | WO 2009/005957 A1 | 1/2009 |

OTHER PUBLICATIONS

Patent Application entitled, "User Interface That Displays Pending and Selected Programming for an Implantable Medical Device," U.S. Appl. No. 12/691,592, filed Jan. 21, 2010.

Patent Application entitled, "User Interface Indicating Fluid Location for an Implantable Fluid Delivery Device," U.S. Appl. No. 12/691,574, filed Jan. 21, 2010.

SynchroMed® II & SynchroMed® EL, Medtronic Reference Card, Bridge Bolus Calculation, Jan. 2008, 2 pages.

SynchroMed® II & SynchroMed® EL, Medtronic Reference Card, Catheter Revision Priming Volume Calculation, Jan. 2008, 2 pages.

SynchroMed® II & SynchroMed® EL, Medtronic Reference Card, Full Catheter Replacement Priming Volume Calculation, Jan. 2008, 2 pages.

SynchroMed® II & SynchroMed® EL, Medtronic Reference Card, Pump Replacement Priming Volume Calculation, Jan. 2008, 2 pages.

SynchroMed® II, Programmable Infusion System Clinical Reference Guide, Intrathecal Baclofen for the Management of Severe Spasticity, 2007, 56 pages, Apr. 2007.

SynchroMed® II, Programmable Infusion System Clinical Reference Guide, Intrathecal Morphine for Pain Management, 2007, 54 pages, May 2007.

SynchroMed® II, Programmable Infusion System Clinical Reference Guide, System Components, 2007, 60 pages, Apr. 2007.

SynchroMed® II, Programmable Infusion System Clinical Reference Guide, Therapy Maintenance, 2007, 79 pages, Apr. 2007.

Smart Card Alliance: News, Personal Health Cards Store Life-Saving Medical Information, Speed Up Hospital Administration: From Smart Card Alliance/CTST Conference, May 19, 2008, 2 pages.

International Search Report and Written Opinion of PCT/US2010/028635, dated Jul. 8, 2011, 17 pp.

Cao et al., "Design and simulation of an implantable medical drug delivery system using microelectromechanical systems technology," Sensors and Actuators A 94 (2001), pp. 117-125.

Galanis et al., "Computer methods for automating preoperative dental implant planning: Implant positioning and size assignment," Computer Methods and Programs in Biomedicine 86, Apr. 2007, pp. 30-38.

* cited by examiner

MANAGEMENT OF SESSION HISTORY DATA FOR IMPLANTABLE FLUID DELIVERY DEVICE

This application claims the benefit of U.S. Provisional Application No. 61/170,363, filed Apr. 17, 2009, which is hereby incorporated by reference in its entirety.

TECHNICAL FIELD

This disclosure relates to implantable medical devices and, more particularly, to programming of implantable medical devices.

BACKGROUND

A variety of medical devices are used for chronic, i.e., long-term, delivery of therapy to patients suffering from a variety of conditions, such as chronic pain, tremor, Parkinson's disease, epilepsy, urinary or fecal incontinence, sexual dysfunction, obesity, spasticity, or gastroparesis. As examples, electrical stimulation generators are used for chronic delivery of electrical stimulation therapies such as cardiac pacing, neurostimulation, muscle stimulation, or the like. Pumps or other fluid delivery devices may be used for chronic delivery of therapeutic agents, such as drugs. Typically, such devices provide therapy continuously or periodically according to parameters contained within a program. A program may comprise respective values for each of a plurality of parameters, specified by a clinician. The devices may be implantable medical devices that receive the program from a programmer controlled by the clinician.

Examples of such implantable medical devices include implantable fluid delivery devices, implantable neurostimulators, implantable cardioverters, implantable cardiac pacemakers, implantable defibrillators, cochlear implants, and others that now exist or may exist in the future. These devices are intended to provide a patient with a therapeutic output to alleviate or assist with a variety of conditions. Typically, such devices are implanted in a patient and provide a therapeutic output under specified conditions on a recurring basis.

One type of implantable fluid delivery device is a drug infusion device configured to deliver a fluid medication to a patient at a selected site. A drug infusion device may be implanted at a location in the body of a patient and deliver a fluid medication through a catheter to a selected delivery site in the body. Drug infusion devices, such as implantable drug pumps, include fluid reservoirs that may be self-sealing and may be accessible through ports. A drug infusion device may be configured to deliver a therapeutic agent from the fluid reservoir to a patient according to a therapy program, which may, for example, specify a rate of delivery by the IMD of a fluid delivered to the patient.

Programmable implantable medical devices are typically programmed using an external instrument, sometimes referred to as a controller or programmer, that communicates with the implanted medical device via wireless telemetry. The programmer can be used by a medical professional to adjust parameters associated with therapy delivered by the implanted medical device. For example, the medical professional may use the programmer to increase or decrease an amount or rate of delivery of fluid medication delivered to the patient. Typically, a medical professional interfaces with the programmer to set various parameters then transmits the parameters to the implanted medical device.

SUMMARY

In general, this disclosure describes techniques for displaying session history data for an implantable fluid delivery device. The session history data may be stored in the implantable fluid delivery device and retrieved by a programmer or other external device for presentation to a user. A programmer may interrogate the implantable fluid delivery device by wireless telemetry to retrieve the stored session history data. The programmer may then display the session history data so that the session history data can be analyzed by a clinician.

In one example, a method includes retrieving, with a device for programming an implantable fluid delivery device, therapy session information for a plurality of therapy sessions administered by the implantable fluid delivery device to a patient, and displaying, with the device, a representation of the plurality of therapy sessions, wherein the representation comprises an abstraction of the therapy session information.

In another example, a programmer device for programming an implantable medical device, such as an implantable fluid delivery device, includes a user interface comprising a display to present a representation of a plurality of therapy sessions administered by an implantable fluid delivery device to a patient, wherein the representation comprises an abstraction of the therapy session information, and a processor that controls the user interface to present on the display the representation of the plurality of therapy sessions.

In another example, a system includes an implantable fluid delivery pump that delivers fluid to a patient according to a selected dosing program, comprising a telemetry module, and a programmer device comprising telemetry module to program the implantable fluid delivery pump, a user interface comprising a display to present a representation of a plurality of therapy sessions administered by the implantable fluid delivery device to a patient, wherein the representation comprises an abstraction of the therapy session information, and a processor that controls the user interface to present on the display the representation of the plurality of therapy sessions.

In another example, a computer-readable medium, such as a computer-readable storage medium, contains, e.g., is encoded with, instructions that cause a programmable processor of a programmer device for programming an implantable fluid deliver device to retrieve therapy session information for a plurality of therapy sessions administered by the implantable fluid delivery device to a patient, and display a representation of the plurality of therapy sessions, wherein the representation comprises an abstraction of the therapy session information.

In another example, a medical device includes means for retrieving therapy session information for a plurality of therapy sessions administered by an implantable fluid delivery device to a patient, and means for displaying a representation of the plurality of therapy sessions, wherein the representation comprises an abstraction of the therapy session information.

The details of one or more examples are set forth in the accompanying drawings and the description below. Other features, objects, and advantages will be apparent from the description and drawings, and from the claims.

BRIEF DESCRIPTION OF DRAWINGS

FIG. 6 is a screenshot illustrating an example user interface screen presented by an external programmer for editing patient information.

FIG. 7 is a screenshot illustrating an example user interface screen presented by an external programmer for editing fluid delivery pump and catheter information.

DETAILED DESCRIPTION

Figure 1:
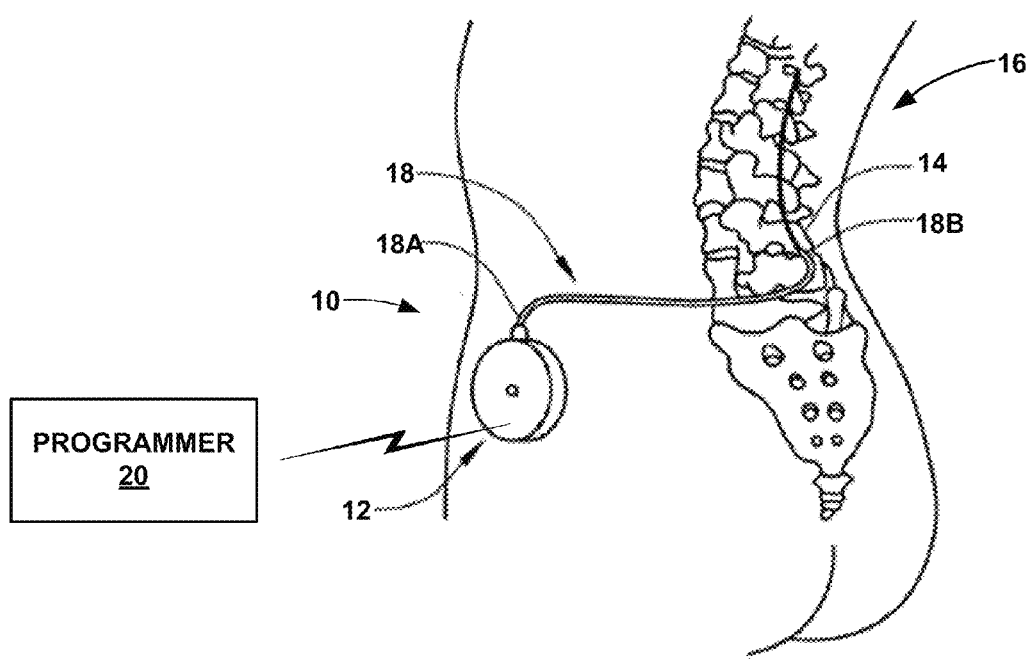
FIG. 1 is a conceptual diagram illustrating an example of a fluid delivery system, which includes an implantable medical device that is configured to deliver a therapeutic agent to a patient via a catheter.

Medical devices are useful for treating, managing or otherwise controlling various patient conditions or disorders, such as, but not limited to, pain (e.g., chronic pain, post-operative pain or peripheral and localized pain), tremor, movement disorders (e.g., Parkinson's disease), diabetes, epilepsy, neuralgia, chronic migraines, urinary or fecal incontinence, sexual dysfunction, obesity, gastroparesis, mood disorders, or other disorders. Some medical devices may be configured to deliver one or more therapeutic agents, alone or in combination with other therapies, such as electrical stimulation, to one or more target sites within a patient. For example, in some cases, a medical device may deliver insulin to a patient with diabetes. The medical device may be implanted in the patient for chronic therapy delivery (e.g., longer than a temporary, trial basis).

In general, this disclosure describes techniques for displaying session history data for an implantable fluid delivery device. The session history data may be stored in the implantable fluid delivery device and retrieved by a programmer or other external device for presentation to a user. A programmer may interrogate the implantable fluid delivery device by wireless telemetry to retrieve the stored session history data. The programmer may also retrieve session history data from local memory of the programmer. The programmer may then display the session history data so that the session history data can be analyzed by a clinician. The session history data may include data for a plurality of previous programming sessions.

The programming session history data may include, for example, an indication of one or more drugs delivered to a patient by the implantable fluid delivery device, one or more dosing patterns for each of the drugs, feedback data recorded by the patient, actions taken during the programming session, configurations of the pump or catheter changed during a clinical visit, diagnostic conditions or events sensed by the device during a given session, or other data associated with a plurality of previous therapy sessions. The clinician may analyze the session history data to determine, for example, effectiveness of a certain drug, effectiveness of a dosing pattern, what drug to administer in the future, a dosing pattern to be administered, whether a current or previous dosing pattern was particularly effective, modifications to the current or previous dosing pattern that would improve the effectiveness of treatment, whether past programming or device configuration actions might explain current patient outcome or symptoms, or other information.

The programmer may present other data, in addition to the session history data, such as patient information, implanted device information such as model, volume, implant location, length of catheter or lead, and other information specific to different devices. Such additional data may be retrieved from the implantable drug pump and presented with the session history data. The session history data and other data may be stored in the implantable medical device. In this manner, the session history data is carried with the patient, and can be retrieved and evaluated by different clinicians, in different clinics, using different programmers.

The techniques of this disclosure further relate to managing, organizing and presenting the session history to a user with a programmer communicatively coupled to the implantable fluid delivery device. The programmer may store the session histories within a programmer memory, store the session histories to a memory of the implantable fluid delivery device, retrieve the session histories from the implantable fluid delivery device, download the session histories from a remote device, merge session history sequences from two or more sources, or retrieve (store) the session histories using other methods and using other devices.

A session history, as used in this disclosure, refers to data relating to one or more therapy sessions. Each session history may include one or more of a type of fluid used to treat the patient, a type of drug or drugs used in the fluid, a total amount of drug administered to the patient during the therapy session, an average amount of drug administered to the patient during each period (e.g., 24 hour period) of the therapy session, a concentration of the drug in the fluid, a dosing program used to administer the fluid during the session, one or more rates at which the implantable fluid delivery device administered the fluid, patient feedback regarding the session, clinician notes regarding the session, device data generated by the implantable fluid delivery device, a catheter length used during the session, an implantation site of the distal tip of the catheter in the patient, a time at which the fluid delivery device was primed, supplemental boluses requested by the patient, supplemental boluses actually delivered to the patient, or other data related to a therapy session.

A therapy session may be defined by the time between successive programming sessions at which a clinician programmed and possibly modified, adjusted, or updated the various programming parameters associated with delivery of the fluid by the implantable drug pump. Some of the programming parameters may define a dosing program. In general, this disclosure uses the term "dosing program" to refer to programming of the implantable fluid delivery device for a particular session. A dosing program may include one or more therapy schedules, each of which may include a plurality of steps, where each step includes a rate at which the implantable fluid delivery device is to administer the fluid and a duration of time over which to administer the fluid at that rate. In some examples, a dosing program may also describe a continuous change in infusion rate from a starting rate at a given time to an ending rate at a final time, rather than a discrete number of steps.

The therapy schedules of a dosing program may correspond to different periods of time, such as a number of hours, a particular day, a plurality of days, or other time periods. For example, a dosing program may include a first therapy schedule for weekdays and a second therapy schedule for weekends. As another example, a dosing program may include an individual therapy schedule for each day of the week. In general, a therapy session corresponds to one dosing program and the clinical actions taken to configure it, although the same dosing program may be applied to a plurality of therapy sessions. The dosing parameters defined within a therapy session may therefore be applied over a number of days, weeks, or even months, between clinician programming sessions. A therapy session may generally include a period of time between programming sessions during which the implantable fluid delivery device administers the dosing program.

In some cases, during a therapy session, a patient may be permitted to adjust some parameters to a limited degree or request supplemental boluses. However, a therapy session generally resides between successive clinician programming sessions. Additionally, data for a therapy session may further include a representation of a one-time event, such as a bridge, prime, therapeutic bolus, or other such one-time events. In some examples, detected events, such as a pump stall, may also form part of the data for a therapy session, and may provide context for any actions taken. In addition, therapy session data may include data relating to configuration changes. Hence, data relating to configuration changes, such as whether the length of a catheter was changed, whether a fluid reservoir was filled or flushed, whether a therapeutic agent was changed, or other similar configuration changes, may also be stored as data for a therapy session.

In this manner, a programmer may present a representation of a plurality of therapy sessions, where the representation comprises an abstraction of the therapy session information. The therapy session information may correspond to the session history data. Each therapy session may be treated as having its own set of therapy session information. The programmer may display an abstraction of the therapy session information by displaying a portion of the therapy session information for each therapy session. The portion that is displayed may be selectable by a clinician or other user. A user may select, for example, average daily dose, relative session end dates, infusion pattern, percent of each dosage that was requested by a patient as a supplemental bolus, type of therapeutic agent, concentration of therapeutic agent, or other available therapy session information as described in greater detail below. In this manner, a user may select the manner in which a set of therapy session information is abstracted for presentation, e.g., by selecting one of several details included in the therapy sessions.

For example, a user may select average daily dose and relative end date for each therapy session, and the programmer may display a plurality of nodes, each of the nodes representative of an average daily dose of therapeutic agent administered during a corresponding therapy session and a relative date on which the corresponding therapy session ended. The therapy session nodes may therefore comprise an abstraction of the therapy session information by representing a portion of the available therapy session information. Although abstraction of therapy session information may be desirable to present a simplified and compact view of a single therapy sessions or multiple therapy sessions, in some cases, a user may be permitted to access additional therapy session information or a complete set of therapy session information by clicking on, hovering on or otherwise manipulating a therapy session node or other media relating to the therapy session node. In this manner, the therapy session node initially presents one or more abstracted details, but may also provide selective access to a more complete set of therapy session details.

Data for a therapy session also may include clinical programming actions taken during a programming session. For example, various one-time events include a bridge, a prime, and a therapeutic bolus may occur during a programming session. An implantable fluid delivery device may be programmed to perform a bridge, e.g., to deliver a bridging bolus, when the device is filled with a new fluid. The new fluid may include a different therapeutic agent, a different concentration of an existing therapeutic agent, additional therapeutic agents (e.g., a plurality of therapeutic agents), or otherwise differ from the current fluid being administered by the device. The implantable fluid delivery device may be programmed to perform a bridge to administer the existing fluid at a rate appropriate for that fluid before administering the new fluid according to a new dosing program. In this manner, the device may be programmed to deliver each of the old fluid and the new fluid according to distinct dosing programs that are suitable for the corresponding one of the fluids. Accordingly, the device may be programmed not to deliver the new fluid according to the old dosing program and not to deliver the old fluid according to the new dosing program. Moreover, the device may automatically switch to the new dosing program from the old dosing program once all of the old fluid has been administered.

A prime is performed when the reservoir of an implantable fluid delivery device is filled with a fluid containing a therapeutic agent for the first time or after the reservoir has been flushed. In general, the device activates a fluid pump within the device to move the fluid to a distal tip of a catheter of the device to perform the prime. The prime ends when the fluid containing the therapeutic agent reaches the distal tip of the catheter.

The implantable fluid delivery device may be programmed to administer a therapeutic bolus or other one-time bolus by a clinician. For example, during a priming phase of the device, the patient generally does not receive any fluid containing the therapeutic agent. The clinician may therefore program the device to administer a therapeutic bolus following a priming phase to provide therapy to the patient following the priming phase. The clinician may also program therapeutic boluses or permit the patient to request therapeutic boluses during the therapy session that are not part of a programmed infusion pattern. Therefore, the term therapeutic bolus may generally refer to any time the implantable fluid delivery device administers fluid outside of a programmed, regularly-scheduled infusion pattern.

The programmer may display data associated with one or more session histories using any or all of the techniques of this disclosure. In general, the programmer may display the data relating to the session histories via a user interface, such as a monitor, in a graphical or textual representation. A graphical representation of the session histories may include a session history trend on a graph that includes a plurality of nodes, where each of the nodes corresponds to one session. Each node may graphically and/or textually represent various aspects of the corresponding session, as described in greater detail below. For example, nodes may be positioned on the graph along the x-axis based on a time at which the session was administered relative to other sessions, and along the y-axis based on a total amount of drug administered to the patient during a therapy session.

In some examples, the shape of a node may represent an infusion pattern of a particular fluid, e.g., a simple continuous pattern may be represented with a circle, a day/night pattern may be represented with a triangle, and an all steps flex pattern may be represented with a square. A simple continuous pattern mode specifies delivery at a constant dosage over a specified period of time, e.g., 24 hours. An all steps flex pattern mode specifies delivery at different dosages at different times during a specified period of time. A day/night pattern mode specifies delivery of different dosages during day and night portions of the specified period of time.

Nodes corresponding to a session that a clinician has annotated may include a symbol, such as a plus sign or a letter, indicating that an annotation exists for that node/session. Such a symbol may also be used to indicate a sensed event or diagnostic condition detected during that session. A user may select an annotated node, e.g., by hovering a mouse pointer over the node or by clicking on the node with a mouse or other user interface device, to view the annotation or details of the sensed event or diagnostic. A node may represent patient feedback with different shading styles, colors, outline styles, or other methods. For example, a node corresponding to a session for which a patient provided negative feedback may be colored red, whereas a node corresponding to a session for which a patient provided positive feedback may be colored green.

A user, such as a clinician, may interact with a programmer to retrieve and view session history information for a particular patient. The user may analyze the session history information for a variety of purposes. For example, the user may use the session history information to better decide how to configure a future session, e.g., what drug to use, what dosing rate to use, what concentration of drug to use, how much drug to administer, whether to allow supplemental boluses to be administered by the patient, how many supplemental boluses to allow, how to modify the dosing program by analyzing when or how often the patient requests supplemental boluses, the time averaged cost of therapy for this patient's current dosing regime, safe maximum and minimum dosing based on historical values, or other configuration options for a pending session. The user may also diagnose a patient's current condition, e.g., when a patient is experiencing withdrawal or overdose symptoms, or other symptoms that could be a response to therapy indicated in a respective session history. In some examples, the user interface may display a representation of cost per unit time of a therapy session, which may inform a user as to a cost for each therapy session, e.g., cost of a therapeutic agent and, based on an infusion pattern, how much will be spent to administer the therapeutic agent according to the infusion pattern.

FIG. 1 is a conceptual diagram illustrating an example of a therapy system 10, which includes IMD 12 configured to deliver at least one therapeutic agent, such as a pharmaceutical agent, insulin, pain relieving agent, anti-inflammatory agent, gene therapy agent, or the like, to a target site within patient 16 via catheter 18, which is coupled to IMD 12. In one example, catheter 18 may comprise a plurality of catheter segments. In other examples, catheter 18 may comprise a unitary catheter. In the example of FIG. 1, the therapeutic agent is a therapeutic fluid. IMD 12 may comprise, for example, an implantable fluid delivery device that delivers therapeutic agents in fluid form to patient 16. In the example shown in FIG. 1, the target site is proximate to spinal cord 14 of patient 16. A proximal end 18A of catheter 18 is coupled to IMD 12, while a distal end 18B of catheter 18 is located proximate to the target site. Therapy system 10 also includes external programmer 20, which wirelessly communicates with IMD 12 as needed, such as to provide or retrieve therapy information or control aspects of therapy delivery, e.g., modify therapy parameters, turn IMD 12 on or off, and so forth. While patient 16 is generally referred to as a human patient, other mammalian or non-mammalian patients are also contemplated.

IMD 12 may have an outer housing that is constructed of a biocompatible material that resists corrosion and degradation from bodily fluids, such as titanium or biologically inert polymers. IMD 12 may be implanted within a subcutaneous pocket close to the therapy delivery site. For example, in the example shown in FIG. 1, IMD 12 is implanted within an abdomen of patient 16. In other examples, IMD 12 may be implanted within other suitable sites within patient 16, which may depend, for example, on the target site within patient 16 for the delivery of the therapeutic agent.

Catheter 18 may be coupled to IMD 12 either directly or with the aid of an extension. In the example shown in FIG. 1, catheter 18 traverses from the implant site of IMD 12 to one or more target sites proximate to spine 14. Catheter 18 is positioned such that one or more fluid delivery outlets of catheter 18 are proximate to one or more target sites within patient 16. IMD 12 delivers a therapeutic agent to one or more target sites proximate to spinal cord 14 with the aid of catheter 18. For example, IMD 12 may be configured for intrathecal drug delivery into an intrathecal space or epidural space surrounding spinal cord 14. The intrathecal space is within the subarachnoid space of spinal cord 14, which is past the epidural space and dura matter and through the theca of spinal cord 14.

Therapy system 10 may be used, for example, to reduce pain experienced by patient 16. IMD 12 may deliver one or more therapeutic agents to patient 16 according to one or more dosing programs that set forth different therapy parameters, such as a therapy schedule specifying programmed doses, dose rates for the programmed dose, and specific times to deliver the programmed doses. In some examples, the therapeutic agent may comprise a liquid. The dosing programs may comprise a part of a program group for therapy, where the group includes a plurality of therapy schedules. In some examples, IMD 12 may be configured to deliver a therapeutic agent to patient 16 according to different therapy schedules on a selective basis. IMD 12 may include a memory to store one or more therapy programs, instructions defining the extent to which patient 16 may adjust therapy parameters, switch between dosing programs, or undertake other therapy adjustments. In accordance with the techniques of this disclosure, IMD 12 may further store one or more session histories in the memory. Patient 16 may select and/or generate additional dosing programs for use by IMD 12 via external programmer 20 at any time during therapy or as designated by the clinician.

In some examples, multiple catheters 18 may be coupled to IMD 12 to target the same or different tissue sites within patient 16. Thus, although a single catheter 18 is shown in FIG. 1, in other examples, system 10 may include multiple catheters or catheter 18 may define multiple lumens for delivering different therapeutic agents to patient 16 or for delivering a therapeutic agent to different tissue sites within patient 16. Accordingly, in some examples, IMD 12 may include a plurality of reservoirs for storing more than one type of therapeutic agent. In some examples, IMD 12 may include a single long tube that contains the therapeutic agent in place of a reservoir. However, for ease of description, an IMD 12 including a single reservoir is primarily discussed herein.

Programmer 20 comprises an external computing device that is configured to wirelessly communicate with IMD 12. For example, programmer 20 may comprise a clinician programmer that the clinician uses to communicate with IMD 12. Alternatively, programmer 20 may comprise a patient programmer that allows patient 16 to view and modify therapy parameters. The clinician programmer may include additional or alternative programming features than the patient programmer. For example, more complex or sensitive tasks may only be allowed by the clinician programmer to prevent patient 16 from making undesired changes to the operation of IMD 12.

Programmer 20 may comprise a hand-held computing device that includes a display viewable by the user and a user input mechanism that can be used to provide input to programmer 20. For example, programmer 20 may include a display screen (e.g., a liquid crystal display or a light emitting diode display) that presents information to the user. In addition, programmer 20 may include a keypad, buttons, a peripheral pointing device, touch screen, voice recognition, or another input mechanism that allows the user to navigate though the user interface of programmer 20 and provide input.

If programmer 20 includes buttons and a keypad, the buttons may be dedicated to performing a certain function, i.e., a power button, or the buttons and the keypad may comprise soft keys that change in function depending upon the section of the user interface currently viewed by the user. Alternatively, the screen (not shown) of programmer 20 may comprise a touch screen that allows the user to provide input directly to the user interface shown on the display. The user may use a stylus or their finger to provide input to the display.

In other examples, rather than being a handheld computing device or a dedicated computing device, programmer 20 may comprise a larger workstation or a separate application within another multi-function device. For example, the multi-function device may comprise a cellular phone, personal computer, laptop, workstation computer, or personal digital assistant that can be configured to an application to simulate programmer 20. Alternatively, a notebook computer, tablet computer, or other personal computer may enter an application to become programmer 20 with a wireless adapter connected to the personal computer for communicating with IMD 12.

When programmer 20 is configured for use by the clinician, programmer 20 may be used to transmit initial programming information to IMD 12. This initial information may include system 10 hardware information such as the type of catheter 18, the position of catheter 18 within patient 16, the type of therapeutic agent(s) delivered by IMD 12, a baseline orientation of at least a portion of IMD 12 relative to a reference point, therapy parameters of therapy programs stored within IMD 12 or within programmer 20, and any other information the clinician desires to program into IMD 12.

The clinician uses programmer 20 to program IMD 12 with one or more dosing programs that define the therapy delivered by IMD 12. During a programming session, the clinician may determine one or more dosing programs that may provide effective therapy to patient 16. Patient 16 may provide feedback to the clinician as to the efficacy of a specific program being evaluated or desired modifications to the dosing program, e.g., via a patient programmer in communication with IMD 12. Once the clinician has identified one or more programs that may be beneficial to patient 16, patient 16 may continue the evaluation process and determine which dosing program or therapy schedule best alleviates the condition of patient 16 or otherwise provides efficacious therapy to patient 16.

The dosing program information may set forth therapy parameters, such as different predetermined dosages of the therapeutic agent (e.g., a dose amount), the rate of delivery of the therapeutic agent (e.g., rate of delivery of the fluid), the maximum acceptable dose, a time interval between successive patient-initiated boluses (e.g., a lock-out interval), a maximum dose that may be delivered over a given time interval, and so forth. IMD 12 may include a feature that prevents dosing the therapeutic agent in a manner inconsistent with the therapy program. Programmer 20 may assist the clinician in the creation or identification of therapy programs by providing a methodical system of identifying potentially beneficial therapy parameters.

A dosage of a therapeutic agent, such as a drug, may be expressed as an amount of drug, e.g., measured in milligrams, provided to the patient over a particular time interval, e.g., per day or twenty-four hour period. This dosage amount may convey to the caregiver an indication of the probable efficacy of the drug and the possibility of side effects of the drug. In general, a sufficient amount of the drug should be administered in order to have a desired therapeutic effect, such as pain relief. However, the amount of the drug administered to the patient should be limited to a maximum amount, such as a maximum daily dose, in order not to avoid potential side effects. Program information specified by a user via programmer 20 may be used to control dosage amount, dosage rate, maximum dose for a given time interval (e.g., daily), or other parameters associated with delivery of a drug or other fluid by IMD 12.

In some cases, programmer 20 may also be configured for use by patient 16. When configured as the patient programmer, programmer 20 may have limited functionality in order to prevent patient 16 from altering critical functions or applications that may be detrimental to patient 16. In this manner, programmer 20 may only allow patient 16 to adjust certain therapy parameters or set an available range for a particular therapy parameter. In some cases, a patient programmer may permit the patient to control IMD 12 to deliver a supplemental, patient bolus, if permitted by the applicable therapy program administered by the IMD, e.g., if delivery of a patient bolus would not violate a lockout interval or maximum dosage limit. Programmer 20 may also provide an indication to patient 16 when therapy is being delivered or when IMD 12 needs to be refilled or when the power source within programmer 20 or IMD 12 need to be replaced or recharged.

Whether programmer 20 is configured for clinician or patient use, programmer 20 may communicate to IMD 12 or any other computing device via wireless communication. Programmer 20, for example, may communicate via wireless communication with IMD 12 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 12 and another programmer via remote telemetry techniques known in the art, communicating via a local area network (LAN), wide area network (WAN), public switched telephone network (PSTN), or cellular telephone network, for example.

Programmer 20 may also include a user interface, such as a display, to display session history information, in accordance with the techniques of this disclosure. For example, programmer 20 may retrieve session history information stored in IMD 12 and display a graphical representation of the session history information, e.g., as a plurality of nodes each corresponding to a therapy session, where each node represents various aspects of the therapy session. When information is stored in an IMD, such as IMD 12, the information may be efficiently available in various scenarios, and can be viewed and used in the same interface as is used for programming. This enables new views of data such as trends of dosing over time, correlations between drugs or outcomes and therapeutic settings, and visualization of the interaction between personal therapy manager (PTM) usage and therapy settings. A patient programmer may present a PTM interface that permits a patient to request delivery of a supplemental bolus on demand, subject to limits such as maximum daily dose, maximum number of supplemental boluses, or lockout intervals between delivery of successive supplemental boluses or regular doses.

Intrathecal delivery was described above. In other applications of therapy system 10, the target therapy delivery site within patient 16 may be a location proximate to sacral nerves (e.g., the S2, S3, or S4 sacral nerves) in patient 16 or any other suitable nerve, organ, muscle or muscle group in patient 16, which may be selected based on, for example, a patient condition. For example, therapy system 10 may be used to deliver a therapeutic agent to tissue proximate to a pudendal nerve, a perineal nerve or other areas of the nervous system, in which cases, catheter 18 would be implanted and substantially fixed proximate to the respective nerve.

As further examples, catheter 18 may be positioned to deliver a therapeutic agent to help manage peripheral neuropathy or post-operative pain mitigation, e.g., with respect to an ilioinguinal nerve or intercostal nerve, gastric therapy for the treatment of gastric motility disorders and obesity, or muscle spasticity or other movement disorders, for mitigation of other peripheral and localized pain (e.g., leg pain or back pain).

As another example, catheter 18 may be positioned to deliver a therapeutic agent to a deep brain site or within the heart (e.g., intraventricular delivery of the agent). Delivery of a therapeutic agent with the brain may help manage any number of disorders or diseases. Example disorders may include depression or other mood disorders, dementia, obsessive-compulsive disorder, migraines, obesity, and movement disorders, such as Parkinson's disease, Alzheimers' disease, spasticity, and epilepsy. Catheter 18 may also be positioned to deliver insulin to a patient with diabetes.

Examples of therapeutic agents that IMD 12 may be configured to deliver include, but are not limited to, insulin, morphine, other pain mitigating pharmaceutical agents, genetic agents, antibiotics, nutritional fluids, analgesics, hormones or hormonal drugs, gene therapy drugs, anticoagulants, proteins, growth factors, cardiovascular medications or chemotherapeutics.

In accordance with techniques described in this disclosure, programmer 20 may display a representation of a plurality of therapy sessions administered by IMD 12 to patient 16. In some examples, at least one of the plurality of therapy sessions includes at least one therapy session for which information was retrieved from IMD 12. That is, programmer 20 may first retrieve therapy session information for at least one therapy session from IMD 12 and then display the retrieved information as part of a displayed session history.

Programmer 20 may also download therapy session information to IMD 12. In some examples, IMD 12 may collect and store therapy session information during a therapy session. For example, IMD 12 may store a number of PTM requests for supplemental boluses, a number of supplemental boluses actually administered, an average daily dose of therapeutic agent or fluid administered to patient 16, a programmed dose of therapeutic agent or fluid to be administered to patient 16, an amount of fluid or therapeutic agent administered to patient 16 as a result of patient-requested supplemental boluses, patient feedback regarding the therapy session, or other data.

By storing data in IMD 12, the techniques of this disclosure may avoid limited access to data, which may result in inefficient availability of data and unavailability of data when a patient moves clinics or presents in an emergency room, as may be the case in some conventional systems. For example, by storing the session history data and other data in IMD 12, the session history data is carried with the patient, and can be retrieved and evaluated by different clinicians, in different clinics, using different programmers.

Figure 2:
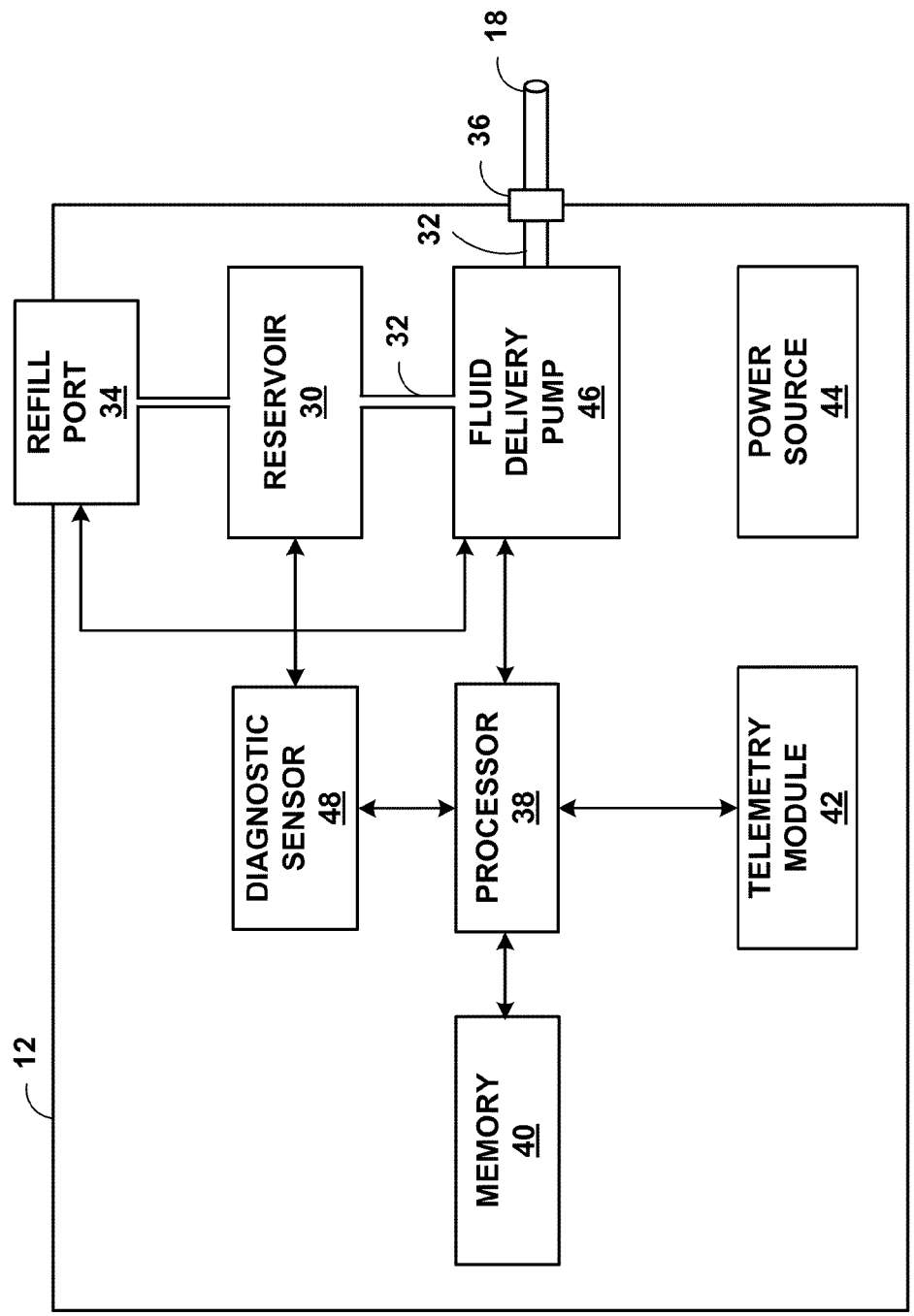
FIG. 2 is functional block diagram illustrating an example of an implantable fluid delivery device.

FIG. 2 is a functional block diagram illustrating components of an example of IMD 12, which includes refill port 34, reservoir 30, processor 38, memory 40, telemetry module 42, power source 44, fluid delivery pump 46, internal tubing 32, diagnostic sensor 48, and catheter access port 36. Fluid delivery pump 46 may comprise a mechanism that delivers a therapeutic agent in some metered or other desired flow dosage to the therapy site within patient 16 from reservoir 30 via the catheter 18. Refill port 34 may comprise a self-sealing membrane to prevent loss of therapeutic agent delivered to reservoir 30 via refill port 34. After a delivery system, e.g., a hypodermic needle, penetrates the membrane of refill port 34, the membrane may seal shut when the needle is removed from refill port 34.

Diagnostic sensor 48 may comprise means for detecting problems, changes, or interactions with one or more of the mechanisms of IMD 12 (for example, refill port 34, reservoir 30, fluid delivery pump 46, catheter access port 36, or catheter 18) or means for detecting clinical actions associated with one of the pump mechanisms (for example, to detect that reservoir 30 was accessed for refill, catheter 18 was accessed via port 36, reservoir 30 was filled/emptied, catheter 18 was revised or changed, etc.). The means for detecting problems, changes, or interactions with these components may comprise one or more pressure sensors. Diagnostic sensor 48 may send a signal to processor 38 upon detecting one or more of these problems, changes, or interactions with the components of IMD 12. In some examples, processor 38 may periodically issue a query to diagnostic sensor 48 to retrieve information collected by diagnostic sensor 48. Processor 38 may store information retrieved from diagnostic sensor 48 in memory 40. In some examples, processor 38 may record in memory 40 that a program revision was downloaded to IMD 12 in the middle of a therapy session, e.g., as a revision to a current dosing program.

In some examples, IMD 12 may have a sensing capability, e.g., diagnostic sensor 48, that can detect diagnostic conditions of the pump hardware and certain clinical actions performed on the pump system. This sensing capability may consist of a plurality of pressure sensors positioned in one or more locations in the fluid delivery path, including refill port 34, reservoir 30, catheter access port 36, fluid delivery pump 46, or a catheter connection. Diagnostic conditions checked by such a pressure sensing system may include the integrity of the catheter (patency, blockage, kinking, or other conditions preventing flow to the tip), the status of the pumping mechanism (missing or extra infusion based on stalls or other mechanical conditions), and the status of the reservoir (over or under pressure conditions). Clinical actions that can be detected based on such a pressure sensing system include insertion of a needle in one of the ports for purposes of refill or catheter access, reservoir filling or aspiration, and catheter connection or disconnection as in a revision surgery or replacement. Inclusion of such detected diagnostic conditions or clinical actions in a therapy session history may improve interpretation of such histories. For instance, a programmed pump priming activity in a case where no catheter aspiration was detected might help explain unexpected patient symptoms or non-optimal therapy outcomes.

Diagnostic sensor 48 may generally detect any or all of the conditions described above. Moreover, diagnostic sensor 48 may send a signal to processor 38 corresponding to the sensed diagnostic condition. Processor 38 may, in turn, store a representation of the sensed diagnostic condition in memory 40, e.g., as part of therapy session data for presentation to a user.

Internal tubing 32 is a segment of tubing that runs from reservoir 30, around or through fluid delivery pump 46, to catheter access port 36. In one example, fluid delivery pump 46 may comprise a squeeze pump that squeezes internal tubing 32 in a controlled manner, e.g., such as a peristaltic pump, to progressively move fluid from reservoir 30 to the distal end of catheter 18 and then into the patient according to parameters specified by a set of program information. Fluid delivery pump 46 may, in other examples, comprise an axial pump, a centrifugal pump, a pusher plate, a piston-driven pump, or other means for moving fluid through internal tubing 32 and catheter 18.

Processor 38 controls the operation of fluid delivery pump 46, e.g., by executing instructions associated with dosing program information stored in memory 40. For example, the instructions may define therapy schedules of a dosing program that each specify the rate at which a therapeutic fluid is to be delivered to a target tissue site within patient 16 from reservoir 30 via catheter 18. The instructions may further specify the time at which the fluid will be delivered and the time interval over which the agent will be delivered at that rate. The amount of the fluid to be delivered is a function of the dosage rate at which the fluid is delivered and the time over which the rate is to be applied. The instructions may be encoded in memory 40, which may comprise a computer-readable storage medium such as, for example, a hard drive or a solid state medium such as a flash drive or memory chip, as described with respect to various examples in greater detail below.

The dosing program may also include other therapy parameters, such as a plurality of therapy schedules, the type of therapeutic agent delivered (if IMD 12 is configured to deliver more than one type of therapeutic agent), concentrations of a drug or drugs in a therapeutic fluid, and so forth. Components described as processors within IMD 12, external programmer 20, or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Memory 40 may include any volatile or non-volatile media, such as a random access memory (RAM), read only memory (ROM), non-volatile RAM (NVRAM), electrically erasable programmable ROM (EEPROM), flash memory, and the like. As mentioned above, memory 40 may store program information including instructions for execution by processor 38, such as, but not limited to, dosing programs, historical dosing programs, timing programs for delivery of fluid from reservoir 30 to catheter 18, and any other information regarding therapy of patient 16. A therapy schedule may indicate the bolus size or flow rate of the drug, and processor 38 may accordingly deliver therapy.

Memory 40 may include separate memories for storing instructions, patient information, therapy parameters, therapy adjustment information, program histories, and other categories of information such as any other data that may benefit from separate physical memory modules or separate memory units. Therapy adjustment information may include information relating to timing, frequency, rates, and amounts of fluid doses or other permitted patient modifications to therapy. In some examples, memory 40 stores program instructions that, when executed by processor 38, cause IMD 12 and processor 38 to perform the functions attributed to them in this disclosure.

Memory 40 may, in some examples, store therapy session information including data relating to a plurality of therapy sessions. When IMD 12 is reprogrammed by programmer 20, all or a portion of a current dosing program may be retained in memory 40 as a historical therapy session. During a therapy session, IMD 12 may record data related to the therapy session in memory 40, such as patient feedback (e.g., related to efficacy of the dosing program), patient-requested supplemental boluses, whether IMD 12 delivered a supplemental bolus in response to the patient's request, clinician notes or comments, or other data.

Telemetry module 42 in IMD 12, as well as telemetry modules in other devices described herein, such as programmer 20, may accomplish communication by RF communication techniques. In addition, telemetry module 42 may communicate with programmer 20 via proximal inductive interaction of IMD 12 with external programmer 20. Accordingly, telemetry module 42 may send information to external programmer 20 on a continuous basis, at periodic intervals, or upon request from the programmer. Processor 38 controls telemetry module 42 to send and receive information. Wireless telemetry may be accomplished by RF communication or proximal inductive interaction of IMD 12 with external programmer 20. In some examples, programmer 20 may retrieve session history information from IMD 12 or download session history information to IMD 12 via telemetry module 42. Telemetry module 42 may also receive signals from a patient programmer device for patient requests for supplemental boluses. Telemetry module 42 may also receive signals from the patient programmer device regarding patient feedback for a current therapy session.

Power source 44 delivers operating power to various components of IMD 12. Power source 44 may include a small rechargeable or non-rechargeable battery and a power generation circuit to produce the operating power. In the case of a rechargeable battery, recharging may be accomplished through proximal inductive interaction between an external charger and an inductive charging coil within IMD 12. In some examples, power requirements may be small enough to allow IMD 12 to utilize patient motion and implement a kinetic energy-scavenging device to trickle charge a rechargeable battery. In other examples, traditional batteries may be used for a limited period of time. As a further alternative, an external inductive power supply could transcutaneously power IMD 12 whenever measurements are needed or desired.

Figure 3:
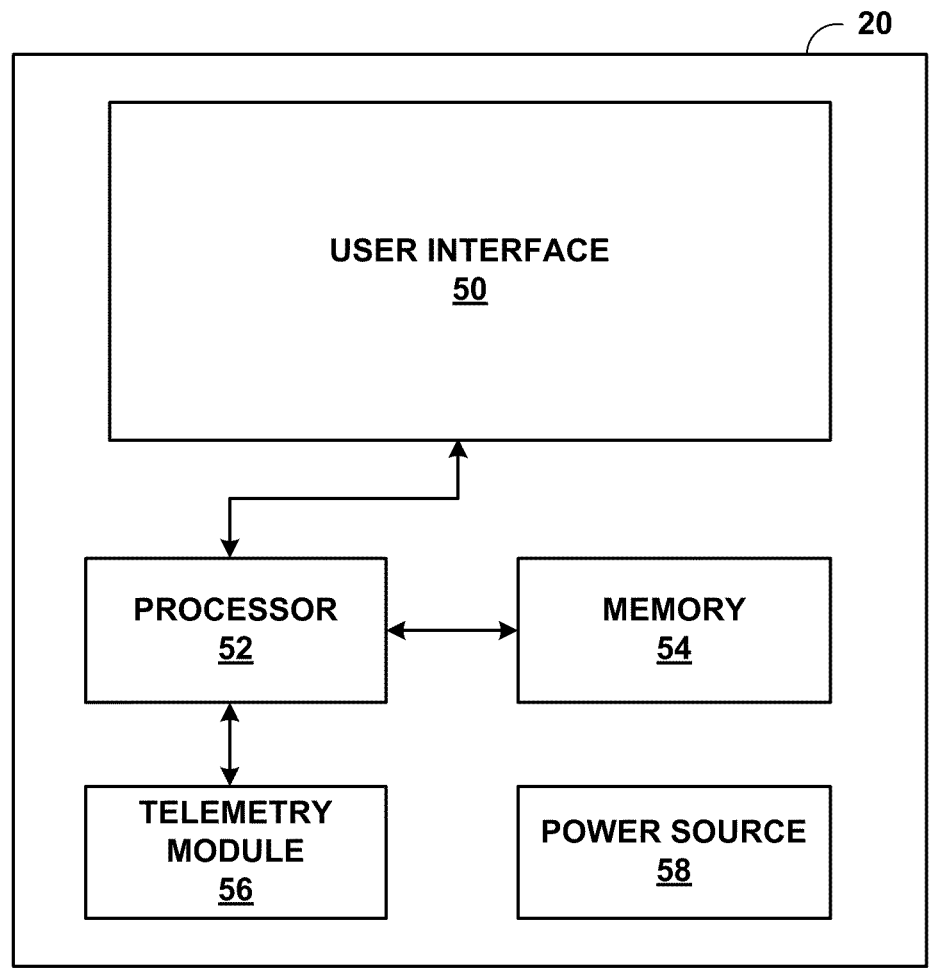
FIG. 3 is a functional block diagram illustrating example components of an external programmer for an implantable medical device.

FIG. 3 is a functional block diagram illustrating various components of an external programmer 20 for IMD 12. As shown in FIG. 3, external programmer 20 includes processor 52, memory 54, telemetry module 56, user interface 50, and power source 58. A clinician or patient 16 interacts with user interface 50 in order to manually change the parameters of a dosing program, change dosing programs within a group of programs, view therapy information, view historical therapy regimens, establish new therapy regimens, or otherwise communicate with IMD 12 or view programming information.

User interface 50 may include a screen and one or more input buttons, as discussed in greater detail below, that allow external programmer 20 to receive input from a user. Alternatively, user interface 50 may additionally or only utilize a touch screen display. The screen may comprise a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like.

Input buttons for user interface 50 may include a touch pad, increase and decrease buttons, emergency shut off button, and other buttons needed to control the therapy, as described above with regard to patient programmer 20. Processor 52 controls user interface 50, retrieves data from memory 54 and stores data within memory 54. Processor 52 also controls the transmission of data through telemetry module 56 to IMD 12. Memory 54 includes operation instructions for processor 52 and data related to patient therapy. That is, memory 54 may be encoded with executable instructions, and processor 52 may be configured to execute the instructions.

User interface 50 may be configured to present therapy program information to the user. User interface 50 enables a user to program IMD 12 in accordance with one or more dosing programs, therapy schedules, or the like. As discussed in greater detail below, a user such as a clinician, physician or other caregiver may input patient information, drug information, therapy schedules, priming information, bridging information, drug/IMD implant location information, or other information to programmer 20 via user interface 50. In addition, user interface 50 may display therapy program information as bar graphs or charts, numerical spread sheets, or in any other manner in which information may be displayed. Further, user interface 50 may present nominal or suggested therapy parameters that the user may accept via user interface 50.

User interface 50 may be configured to display a representation of a plurality of therapy sessions administered by IMD 12 to patient 16. As described in greater detail below, user interface 50 may display a representation of session history information regarding IMD 12, or a plurality of IMDs, for patient 16. User interface 50 may, in various examples, display any or all of the example user interface screens of FIGS. 4-22. By displaying a representation of a session history, programmer 20 may enable a clinician or other user to reconstruct the history to determine a cause of certain events. For example, when a patient presents symptomatic side effects, signs of over- or under-dose, signs of withdrawal, or other symptoms, the user may refer to the session history representation to determine a cause for the symptoms.

Telemetry module 56 allows the transfer of data to and from IMD 12. Telemetry module 56 may communicate automatically with IMD 12 at a scheduled time or when the telemetry module detects the proximity of IMD 12. Alternatively, telemetry module 56 may communicate with IMD 12 when signaled by a user through user interface 50. To support RF communication, telemetry module 56 may include appropriate electronic components, such as amplifiers, filters, mixers, encoders, decoders, and the like. Power source 58 may comprise a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 12 in addition to programming IMD 12. Alternatively, a recharging device may be capable of communication with IMD 12. Then, the recharging device may be able to transfer programming information, data, or any other information described herein to IMD 12. In this manner, the recharging device may be able to act as an intermediary communication device between external programmer 20 and IMD 12. Communicated data described by this disclosure may be communicated between IMD 12, programmer 20, and the recharging device via any type of external device capable of communication with IMD 12.

In this manner, external programmer 20 is an example of a programmer device that includes a user interface comprising a display to present a representation of a plurality of therapy sessions administered by an implantable fluid delivery device to a patient, wherein the representation comprises an abstraction of therapy session information for the plurality of therapy sessions and a processor that controls the user interface to present on the display the representation of the plurality of therapy sessions.

Figure 4:
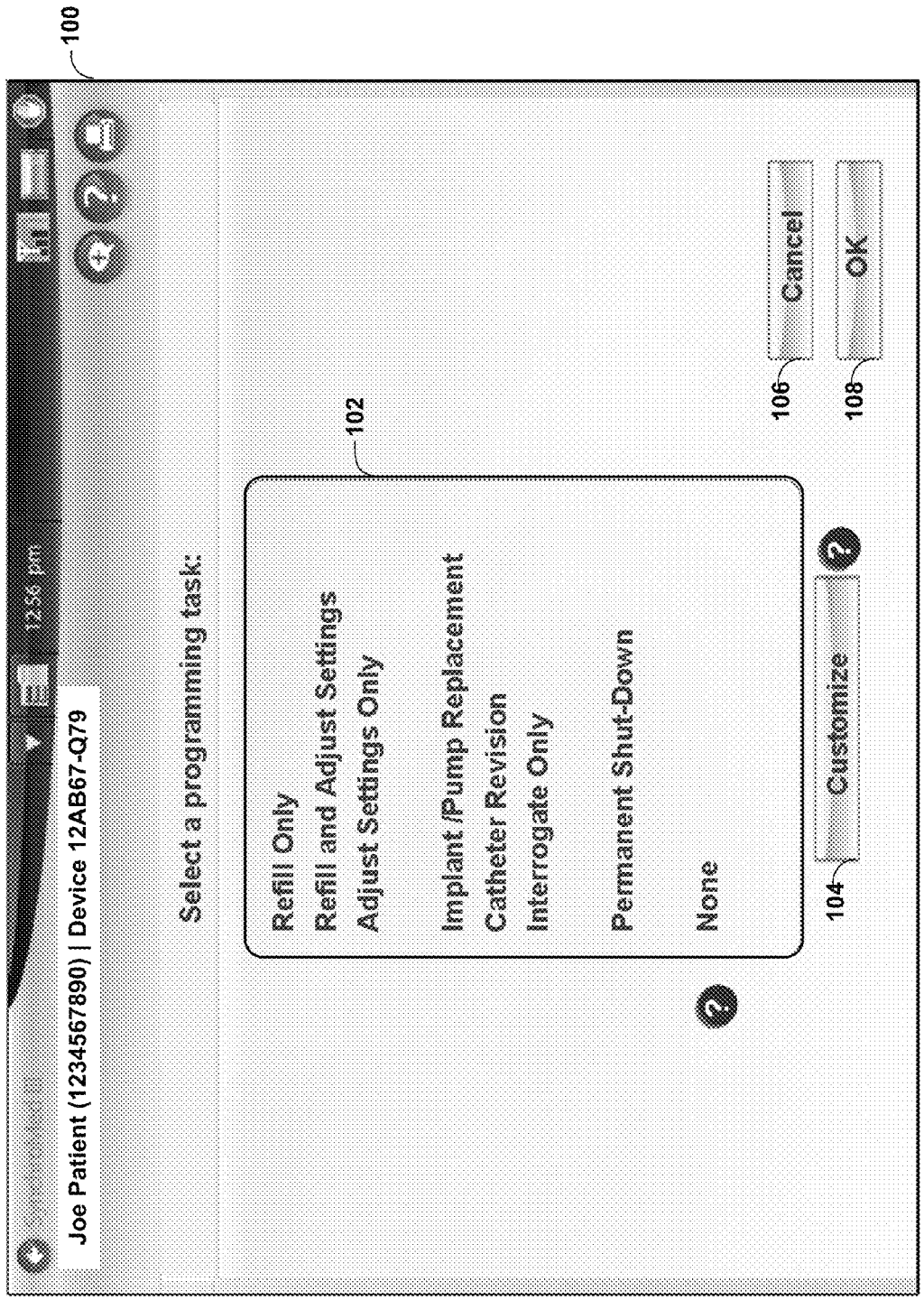
FIG. 4 is a screenshot illustrating an example user interface screen presented by an external programmer when a user first begins interacting with the programmer.

FIG. 4 is a screenshot illustrating an example user interface screen 100 presented by programmer 20 when a user interacts with programmer 20. User interface screen 100 may be displayed by user interface 50 of programmer 20. When a user begins a session of working with programmer 20, programmer 20 presents user interface screen 100 to the user. The user may select from a variety of tasks 102 to perform using programmer 20. Tasks 102 of FIG. 4 depict example tasks "refill only," "refill and adjust settings," "adjust settings only," "implant/pump replacement," "catheter revision," "interrogate only," "permanent shut-down," and "none." Other examples of user interface screen 100 may include additional or fewer tasks for the user to perform.

In one example, processor 52 determines, from the selection of tasks 102, a series of task screens to present to the user of programmer 20 via user interface 50. Processor 52 may cause user interface 50 to present one or more task screens, each of which may receive one or more pieces of data from the user, in order to program IMD 12 according to the selected one of tasks 102. Programmer 20 may implement more task screens than are necessary for any one of tasks 102, therefore programmer 20 may not display unnecessary screens to the user. In this manner, programmer 20 may assist a user in efficiently programming IMD 12 by requesting relevant data without requesting unnecessary data. Programmer 20 may therefore minimize the number of screens that are displayed based on a selection from tasks 102.

The user may select one of tasks 102 from user interface screen 100. For example, the user may select one of the tasks using a pointer controlled by a mouse. As another example, the user may select one of the tasks by touching the task on a touch-screen interface, e.g., with a finger or a stylus. The user may select Cancel button 106 to end the current session or, after selecting one of tasks 102, the user may select OK button 108 to perform the task. Upon receiving a selection of OK button 108, the user interface presents a different display screen to enable the user to perform the task with programmer 20. The user may also select Customize button 104 to customize the task selected from list 102, e.g., one or more parts or sub-parts of the task selected from list 102. In this manner, the user may select which of the one or more task screens are displayed.

Figure 5A:
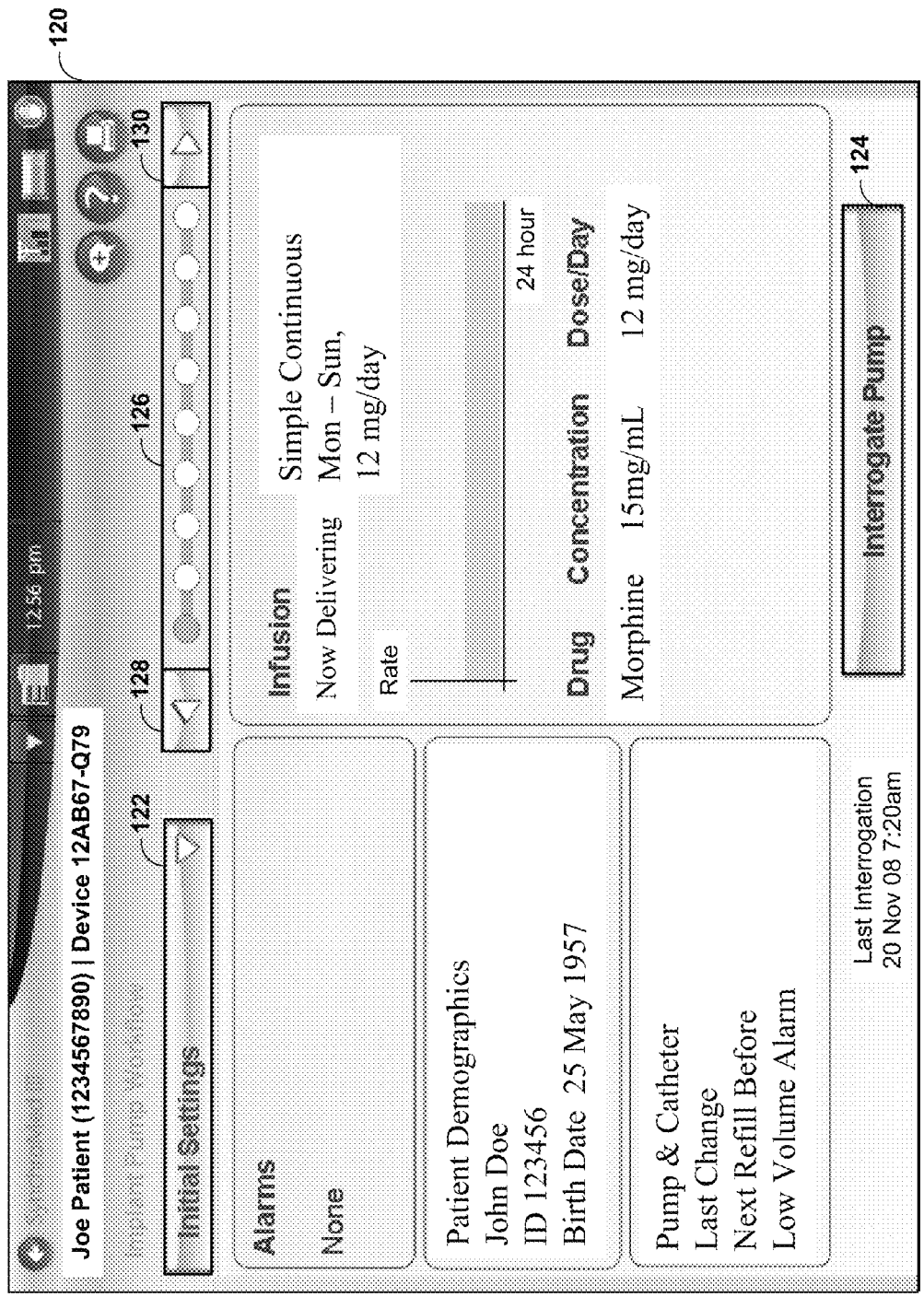
FIGS. 5A and 5B are screenshots illustrating an example user interface screen presented by an external programmer for configuring an implantable medical device.
Figure 5B:
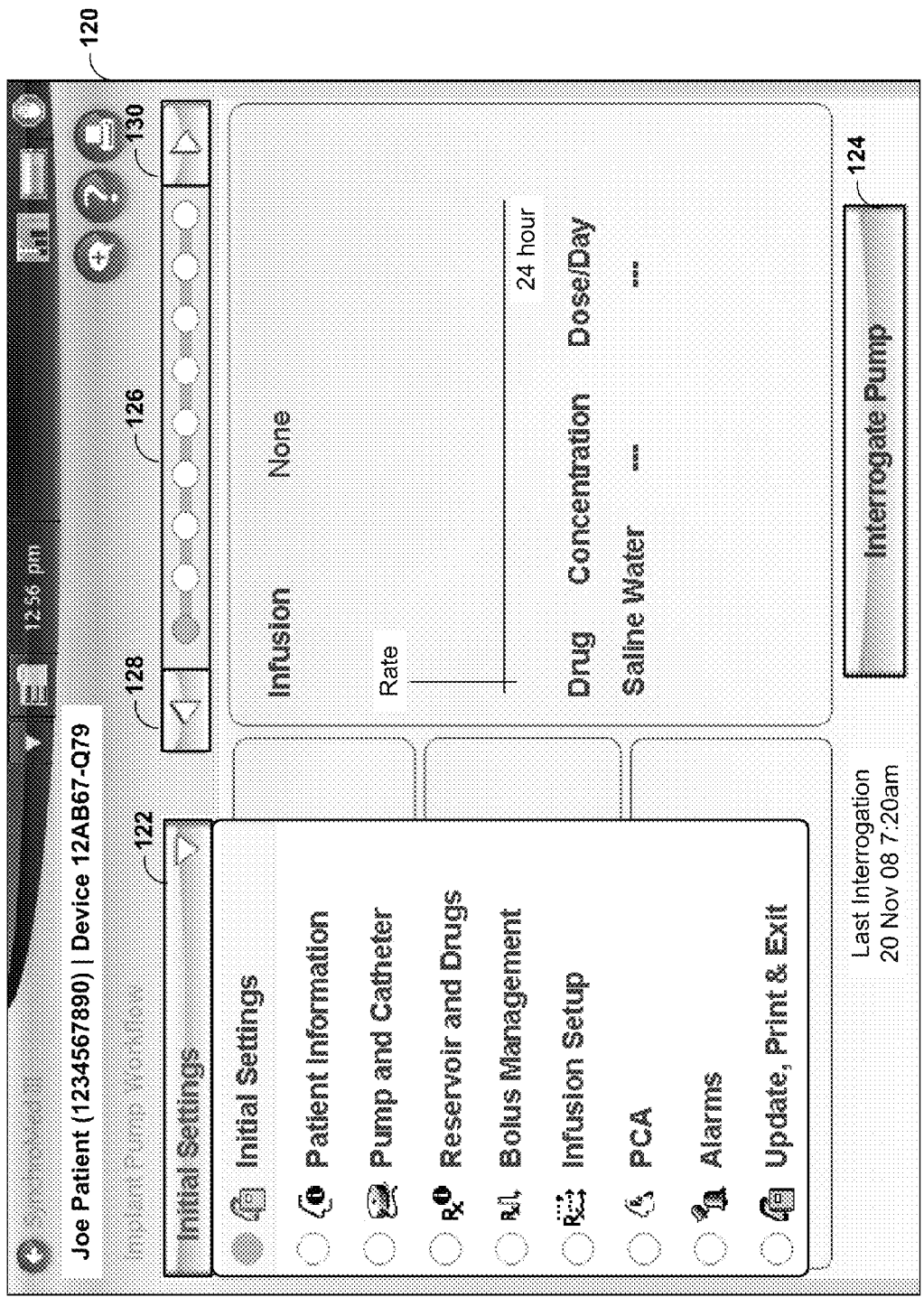

FIGS. 5A and 5B are screenshots illustrating an example user interface screen 120 for configuring IMD 12. User interface screen 120 may be displayed by user interface 50 of programmer 20. User interface screen 120 may be displayed, e.g., when a user selects the "implant/pump replacement" task from tasks 102 and then selects OK button 108 of user interface screen 100 (FIG. 4). FIG. 5A depicts current information for the current settings of an IMD, such as IMD 12, associated with the program. For example, the information includes alarms, patient demographics, pump and catheter information, drug information, and an infusion pattern in the example of FIG. 5A. The user may select Interrogate Pump button 124 to populate programmer 20 with data stored on IMD 12. The user may elect to do this when IMD 12 stores current patient data, but programmer 20 does not store current patient data. For example, IMD 12 may have been programmed with a different programmer than programmer 20, and possibly programmed at a different clinic. The user may also select Interrogate Pump button 124 to retrieve data from IMD 12 that IMD 12 has collected during operation within patient 16, e.g., with one or more previous therapy sessions, i.e., operational periods between successive programming sessions.

The user may edit settings of the program by selecting various options from drop-down menu 122. FIG. 5B illustrates various example options, including "initial settings," "patient information," "pump and catheter," "reservoir and drugs," "bolus management," "infusion setup," "PCA," "alarms," "review history," "session history," and/or "update, print, and exit." When a user selects any of these options from drop-down menu 122, programmer 20 updates and refreshes user interface screen 120 to illustrate settings and options for the selected option.

FIGS. 5A and 5B also include programming status indicator 126, left navigation arrow 128, and right navigation arrow 130. Programming status indicator 126 informs the user of where the user is in the programming process, e.g., in the process of developing a pending dosing program for IMD 12. Processor 52 may, according to instructions encoded within memory 54 of programmer 20, determine which screens are necessary to program IMD 12 based on input received with the example user interface of FIG. 4. The user may also navigate between screens using left navigation arrow 128 and right navigation arrow 130. In addition, the user may jump to a particular screen by selecting the screen from drop-down menu 122. When the user selects left navigation arrow 128, processor 52 may cause user interface screen 120 to display a previous screen in the process of programming IMD 12.

Similarly, when the user selects right navigation arrow 130, processor 52 may cause user interface screen 120 to display a next screen in the process of programming IMD 12. Status indicator 126 may indicate whether the user has entered sufficient information in each screen, which screen the user is currently viewing, how many screens are remaining, or other information regarding the programming status of IMD 12. Information about which screens (e.g. clinical tasks) a user performed during a programming session may be saved and stored as part of the history information for a session history entry. Such information may be of value in reconstructing previous session activities when troubleshooting an unexpected outcome. For example, processor 52 may store identifications for one or more programming screens in memory 54 with which a user interacted for a particular programming session.

Figure 6:
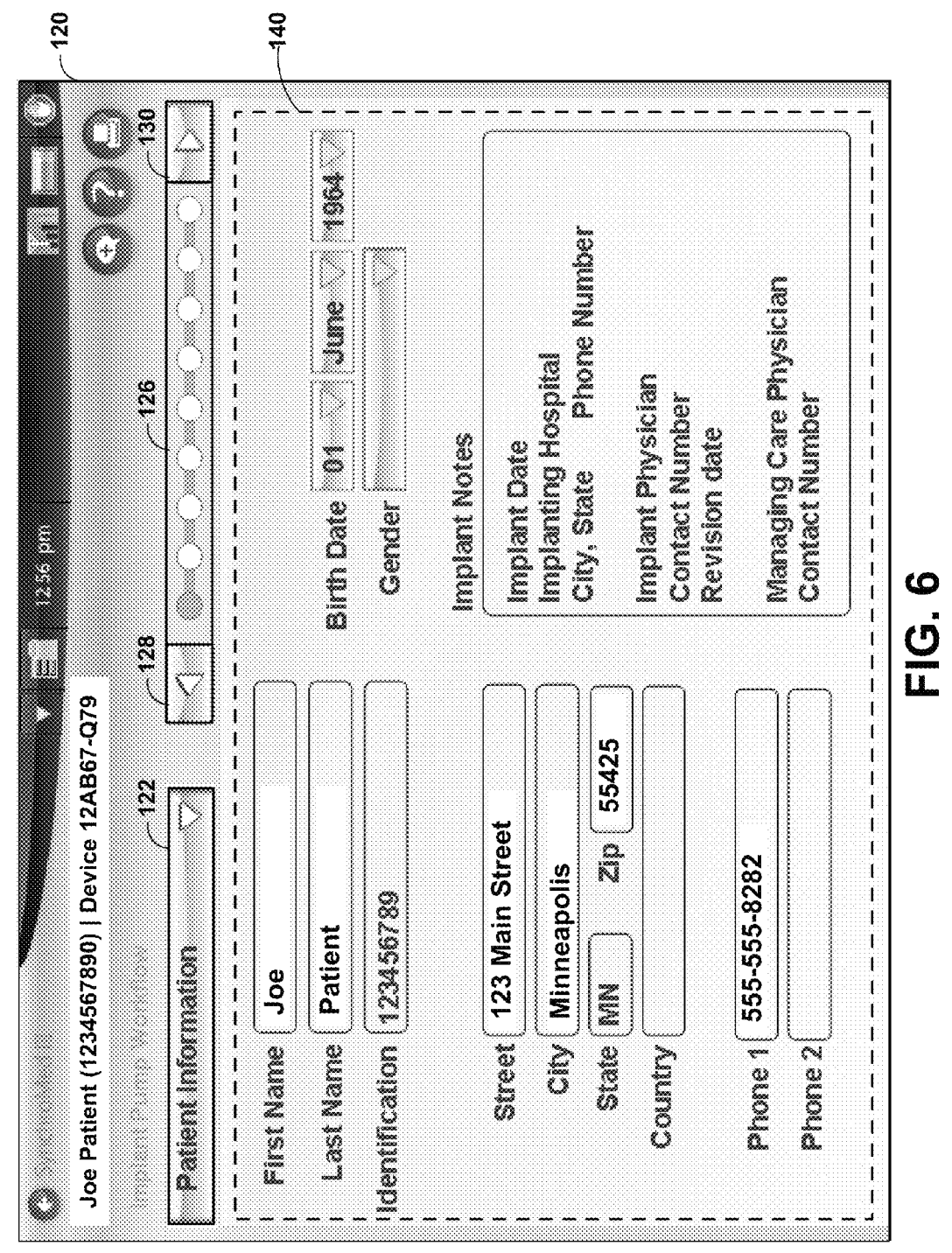

FIG. 6 is a screenshot illustrating an example user interface screen 120 for editing patient information 140. User interface screen 120 displays patient information 140 when a user selects "patient information" from drop-down menu 122. The user fills in fields of patient information 140 to save patient data to memory 54 of programmer 20, such that the patient information can be retrieved at a later time. This information may also assist the user in selecting a therapy regimen for patient 16.

Figure 7:
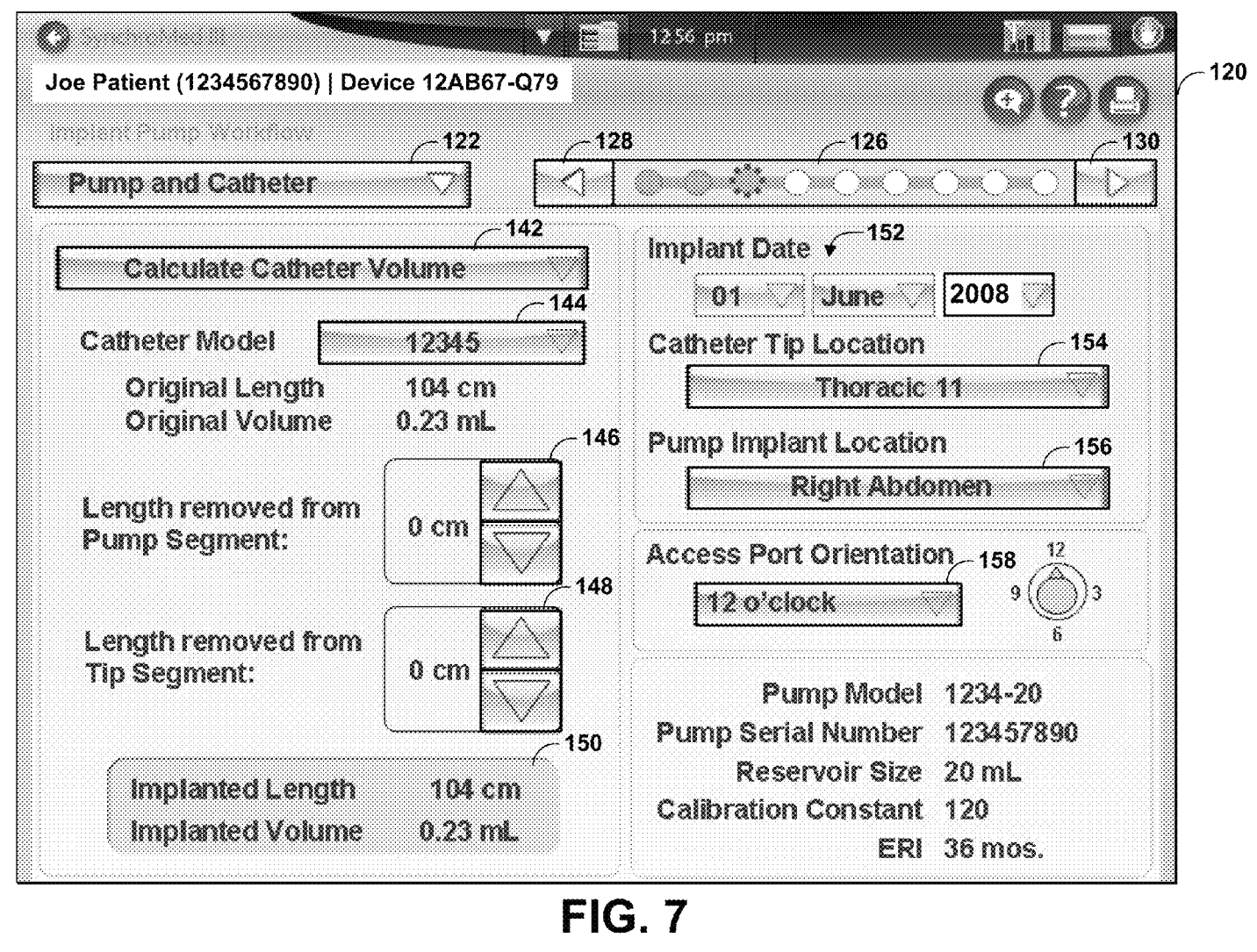

FIG. 7 is a screenshot illustrating an example user interface screen 120 for editing drug pump and catheter information. User interface screen 120 displays information for editing drug pump and catheter information when the user selects "pump and catheter" from drop-down menu 122. For example, user interface screen 120 enables a user to describe catheter volume, a date of implantation of IMD 12, a location of IMD 12, and other information regarding IMD 12.

The user can select various methods for entering catheter volume from catheter volume drop-down menu 142. In the example of FIG. 7, the user has selected "calculate catheter volume," which causes programmer 20 to calculate the catheter volume from various data regarding the catheter, such as length and diameter. In another example, the user may select "enter catheter volume" from drop-down menu 142, e.g., when the user knows the volume of the catheter and desires to enter the volume directly, rather than having programmer 20 calculate the volume. In the example of FIG. 7, the user selects a catheter model from catheter model drop-down menu 144.

Programmer 20 may store default values for potential catheter models for the catheter's length and volume before the catheter has been modified. Changes to catheter values may be especially valuable to store as part of the information in a session history, as they are very impactful to certain programming operations such as bridging from one drug to another or priming the system's tubing. Knowledge of such changes might be important to correctly interpret other information in the history, such as dosing changes. In some examples, programmer 20 may store information regarding a catheter length or changes to a catheter length for catheter 18 of IMD 12 in memory 54.

Programmer 20 may, for example, store information regarding a starting length of catheter 18, a length of catheter 18 that was removed, an ending length of catheter 18 (calculated from the starting length minus the length removed, or as reported by a clinician), a priming volume for catheter 18 (i.e., an amount of fluid pumped by IMD 12 to move the fluid to the distal tip of catheter 18), or other information regarding catheter 18. User interface 120 may also display one or more representations of this information.

When drug pump IMDs are implanted in patients, surgeons commonly remove one or more segments from the catheter of the IMD. To determine a proper bolus amount for priming, the surgeon who removed this segment from the IMD must record the length of the segment removed. The user of programmer 20 may therefore enter the length of the segment removed from the catheter using user interface screen 120 by selecting the length removed from the pump segment with arrows 146 and the length removed from the tip segment with arrows 148. When user interface screen 120 receives removed-length data from arrows 146 and 148, user interface screen 120 sends the data to processor 52, which calculates a resulting length for the catheter, as well as a resulting volume for the catheter, e.g., in accordance with a program or module stored in memory 54. The processor then returns the results to be displayed to user interface screen 120, and user interface screen 120 displays the resulting length and the resulting volume for the catheter in output box 150.

User interface screen 120 also allows a user to enter a date that IMD 12 was implanted with boxes 152. The user also enters a location where the tip of catheter 18 of IMD 12 was implanted using drop-down menu 154, as well as a location of IMD 12 itself using drop-down menu 156. A subsequent user of programmer 20 may therefore determine the location of IMD 12, e.g., to refill reservoir 30 of IMD 12 with fluid. The user also enters the orientation of the access port using drop-down menu 158. The orientation of the access port assists a user in determining the location and orientation of refill port 26 of IMD 12.

Figure 8:
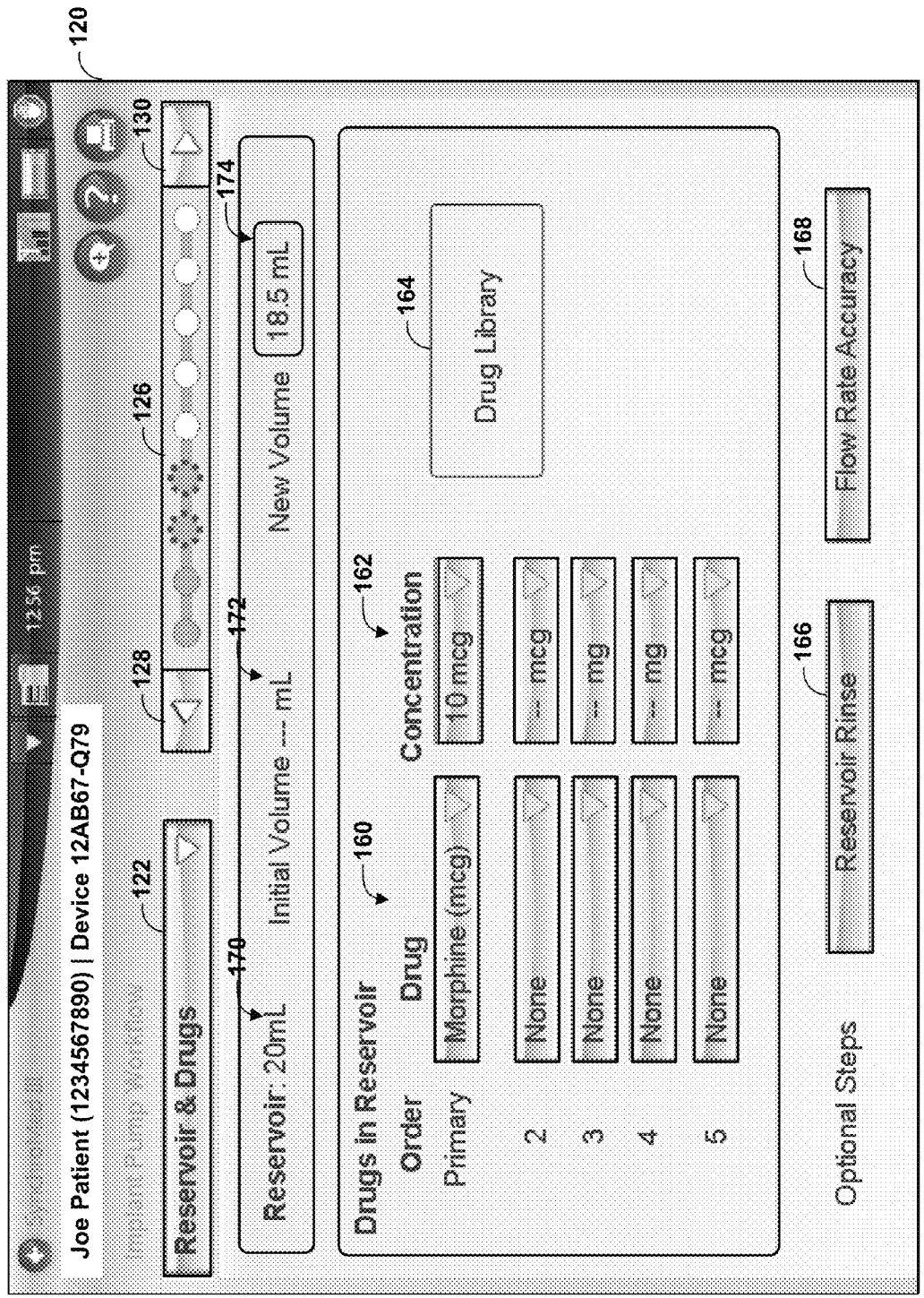
FIG. 8 is a screenshot illustrating an example user interface screen presented by an external programmer for editing drug information regarding a drug delivered by an implantable medical device.

FIG. 8 is a screenshot illustrating an example user interface screen 120 for editing drug information regarding a drug delivered by IMD 12. User interface screen 120 enables a user to modify drug information for drugs delivered by IMD 12. Therefore, when a subsequent user interrogates IMD 12, the subsequent user may determine the information regarding the drug delivered by IMD 12.

User interface screen 120 depicts reservoir information that indicates a maximum volume 170 of reservoir 30 of IMD 12, a starting or initial volume 172 of drug within reservoir 30 as of the time of the programming session, and a new volume 174 that will be inserted into reservoir 30 after the programming session has been completed. In one example, IMD 12, programmer 20, or both, determine initial volume 172 at the beginning of a programming session by subtracting the dispensed volume of drug delivered to patient 16 since the last programming session from the new volume 174 entered at the time of the last programming session. The dispensed volume can be determined by multiplying the rate of drug delivery (volume/time) by the amount of elapsed time drug was dispensed at that rate.

The user may also enter drug information into drug selection area 160 and concentration selection area 162. The user may select a drug from a drop-down menu of drug selection area 160 that is to be delivered to reservoir 30 of IMD 12. The user may also select a corresponding concentration of the drug from a corresponding drop-down menu of concentration selection area 162. Example drugs that may be listed by drop-down menus of drug selection area 160 include saline (as a default filler or as a placebo during clinical testing or other drug trails), morphine, bupivacaine, clonidine, hydromorphone, baclofen, alpha adrenergic agonists, baclofen, fentanyl, sufentanil, ziconotide, or other drugs or fluids. Selecting drugs from multiple drop-down menus of drug selection area 160 indicates that a combination of drugs is to be delivered to reservoir 30. For example, a user may select "morphine" from a first drop-down menu and "bupivacaine" from a second drop-down menu of drug selection area 160.

The user may also select Drug Library 164 to link to a drug library. User interface screen 120 may then display Drug Library information, such as a list of drugs and information regarding each of the listed drugs, such as names of the drugs, one or more common concentration values, and units for the values. In one example, the user may select a drug from the drug library, including a concentration of the drug, and user interface screen 120 populates one or more of drop-down menus 160 and/or 162 with the user's selection. The user may also perform optional steps during the programming session, such as performing a reservoir rinse to rinse reservoir 30 of IMD 12 by selecting reservoir rinse button 166 or determining flow rate accuracy of IMD 12 by selecting flow rate accuracy button 168.

Figure 9:
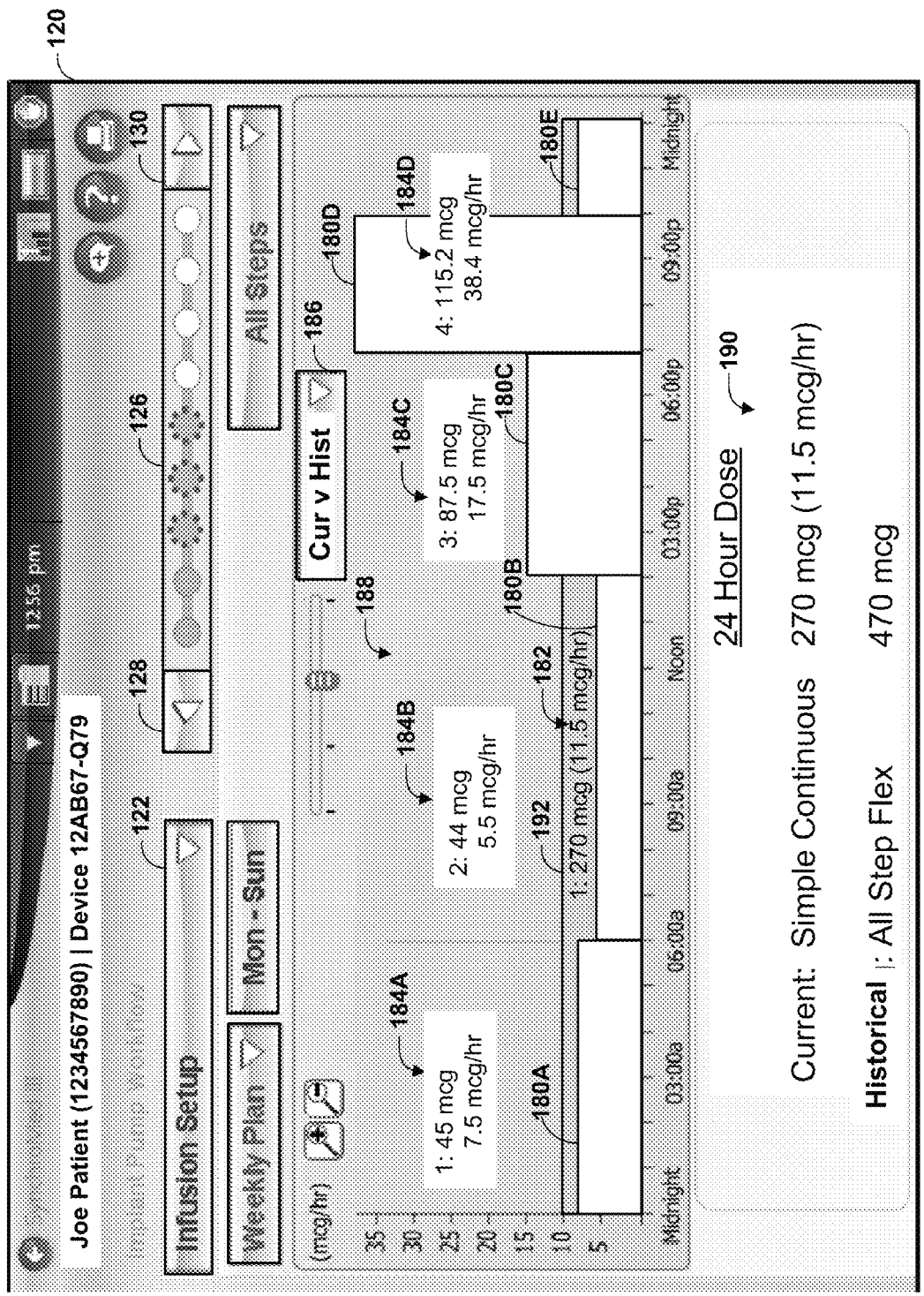
FIG. 9 is a screenshot illustrating an example user interface screen for displaying current dosage information for a current dosing program simultaneously with historical dosage information for a historical dosing program.

FIG. 9 is a screenshot illustrating an example user interface for displaying a therapy schedule of a current dosing program simultaneously with a therapy schedule of a historical dosing program, i.e., a dosing program administered during a previous therapy session. That is, processor 52 may cause user interface screen 120 to display a representation, such as the example of FIG. 9, of a current dosing program, i.e., a dosing program according to which IMD 12 is currently administering a therapy, and simultaneously display a representation of a historical dosing program, i.e., a dosing program according to which IMD 12 has previously administered a therapy. In particular, in the example of FIG. 9, step 192 corresponds to a current dosing program while steps 180A-180E (steps 180) correspond to a historical dosing program. Step 192 provides an indication of a therapy schedule of the current dosage program, while steps 180 represent a therapy schedule of the historical dosing program.

To display graph 188, which includes step 192 and steps 180, the user may select "Cur v Hist" (current vs. historical) from display selection drop-down menu 186. Processor 52 then causes user interface screen 120 to display, e.g., a graphical representation of a current dosing program (or infusion pattern) and a graphical representation of a historical dosing program (or infusion pattern) simultaneously. Drop-down menu 186 may include other options, such as "current" to display a representation of the current dosing program or a therapy schedule of the current dosing program of IMD 12, and "historical" to display a historical dosing program or a therapy schedule of the historical dosing program. User interface 120 may present a dialog box by which a user may select which of a plurality of historical dosing programs to display.

Graph 188 may provide graphical representations of both the current dosing program (i.e., step 192) and the historical dosing program (i.e., steps 180). In addition, user interface screen 120 may provide textual representations of the dosing programs. For example, user interface screen 120 illustrates textual representation 182, corresponding to step 192. User interface screen 120 also illustrates textual representations 184A-184D, corresponding to steps 180A-180D. User interface screen 120 also may provide textual representations of the style of infusion pattern for each of the dosing programs: text representation 266 ("Simple Continuous") for the current (i.e., initial) dosing program 192 and text representation 268 ("All Step Flex") for the historical dosing program. Simple Continuous may refer to a dosing program that specifies delivery of a drug at a constant rate throughout a 24 hour time period. All Step Flex may refer to a dosing program that specifies delivery of a drug at different rates at particular times during the 24 hour time period.

User interface screen 120 also may provide summary textual representation 190, which summarizes differences between the current dosing program and the historical dosing program. In this manner, summary textual representation 190 may provide an abstraction of available therapy session information. In the example of FIG. 9, summary textual representation shows that for the 24-hour dosage period, the current dosing program provides 270 mcg of drug at 11.5 mcg/hour, while the historical dosing program provided 470 mcg of drug.

User interface screen 120 may represent differences between the current dosing program and the historical dosing program in a variety of ways. For example, user interface screen 120 may illustrate the current dosing program (e.g., step 192) with a first color and the second dosing program (e.g., steps 180) with a second color. Other distinguishing features may include line styles, opacity or transparency, shading, hatching, or other means for distinguishing two graphs.

In one example, processor 52 may calculate a difference between a rate represented by a first step of a first dosing program and a rate represented by a second step of a second dosing program, where both the first step and the second step occur at the same temporal location in an application time period (e.g., 24 hour period), and user interface screen 120 may display the calculated difference as an absolute difference, as a percentage difference, with a colored band (e.g., green for increase and red for decrease, different colors to represent different percentage changes, etc.), arrows to represent increase or decrease, varying line thickness, or other visual queues to represent the difference.

Additionally, in some examples, more than two dosing programs may be displayed in this fashion, with each additional historical program displaying as yet another layer with its own distinguishing feature. In the case where multiple historical views are provided, the distinguishing features may be arranged so as to provide information regarding the sequence in time. For instance, user interface 120 may display the oldest historical view with the darkest color or shading and the newest historical view with the lightest color or shading, the oldest may be more transparent and the newest less transparent, or other visual cues may be used to indicate relative age of the historical views.

Figure 10:
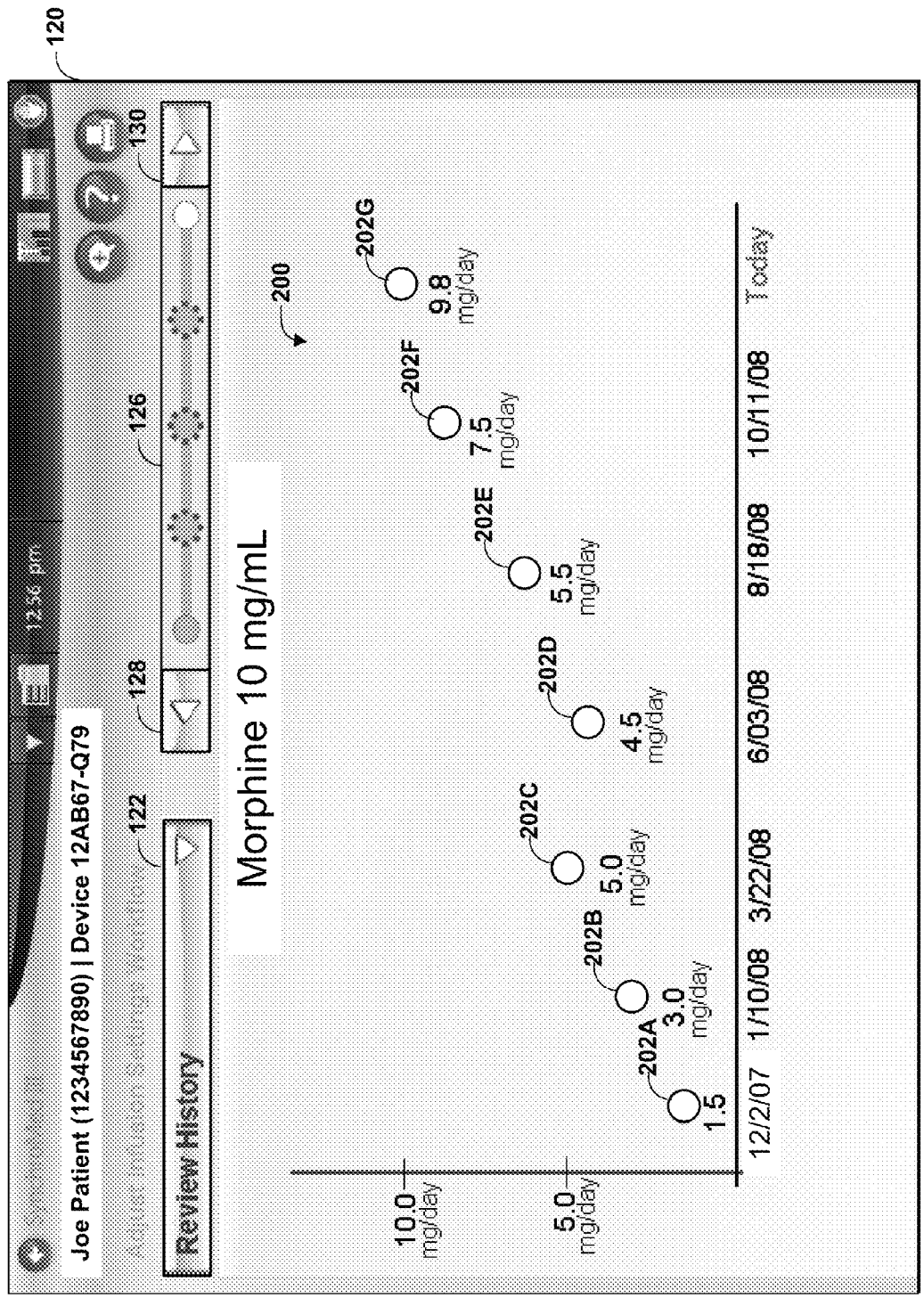
FIG. 10 is a screenshot illustrating an example user interface for displaying a graphical trend of session history information.

FIG. 10 is a screenshot illustrating an example user interface for displaying a graphical trend of session history information. Processor 52 may cause user interface 120 to display graph 200 when a user selects "Review history" from drop-down menu 122. Graph 200 includes nodes 202A-202G (nodes 202) that each represent information regarding a corresponding therapy session. Each therapy session corresponds to a period of time between successive programming sessions during which IMD 12 delivers therapy to the patient according to one or more specified dosing programs. Successive programming sessions may refer to successive clinic visits by the patient, successive remote programming sessions (e.g., over a remote network connection), or other events at which the programming of IMD 12 was changed, updated, or adjusted by a clinician.

Although nodes 202A-202G are depicted in the example of FIG. 10, it should be understood that in other examples, user interface 120 may display a number (0-N) nodes, based on a number of available therapy sessions, and based on a maximum number of nodes to display. In some examples, additional nodes may be represented off screen, and user interface 120 may display a horizontal scroll bar (not shown) that allows a user to move the display along the x-axis to view the additional nodes. Alternatively, the orientation of display screen 120 may be such that different therapy sessions are shown at respective positions along a vertical axis, rather than a horizontal access. Accordingly, the orientation presented in FIG. 10 is provided for purposes of illustration, and should not be considered limiting.

In some examples, processor 52 may cause user interface 120 to display a plurality of trends, where each of the plurality of trends corresponds to one of a plurality of fluids, therapeutic agents, infusion patterns, or other information for a particular therapy session. In the case where a plurality of trends are displayed, user interface 120 may display the plurality of trends on the same set of axes or may display each of the plurality of trends on their own axes with units appropriate to the individual data set being trended. In any case, respective nodes may be presented for each of the therapy sessions. User interface 120 may present a line or curve that interconnects the nodes, thereby facilitating interpretation of trend information.

Each of nodes 202 represents information regarding a corresponding therapy session. In the example of FIG. 10, a location along the x-axis of a particular one of nodes 202 corresponds to a date or relative date on which the therapy session ended. A location along the y-axis of the one of nodes 202 corresponds to an average daily dose of a therapeutic agent administered to patient 16 by IMD 12 during the therapy session. In one example, the average daily dose may comprise a daily average for each day of the therapy session. In another example, a user may select individual days of the week, such as weekdays, weekends, or selected individual days, for which processor 52 may calculate average daily doses.

For example, if the patient regularly performs strenuous exercise on particular days of the week, and therefore receives additional doses of a therapeutic agent during those days only, the clinician may request to exclude those days from the calculation of the average daily dose to view an average daily dose for "normal" days during the therapy session, i.e., days that do not include the strenuous exercise. The clinician may also select the days on which the patient performs the strenuous exercise to view an average daily dose for days on which the patient performs strenuous exercise. In some examples, a location along the y-axis may correspond to a programmed daily dose of the therapeutic agent or a fluid. Node 202A, for example, represents a therapy session that ended on Dec. 2, 2007, during which 1.5 mg of morphine was administered to patient 16 per day. As another example, node 202B represents a therapy session that ended on Jan. 10, 2008, during which 3.0 mg of morphine was administered to patient 16 per day.

In this manner, user interface 120 may display a representation comprising a plurality of temporally-ordered nodes representative of individual therapy sessions. The nodes may also therefore comprise an abstraction of therapy session information. Moreover, user interface 120 may also simultaneously display representations for a plurality of distinct therapy sessions. Each of the nodes may represent only a subset of all of the available information for the corresponding therapy session. In some examples, as discussed below, a user may select a node for a particular therapy session to drill down into and extract additional information for the therapy session corresponding to the selected node. For example, a user may select a node, e.g., by clicking on one of nodes 202, and user interface 120 may retrieve additional information for the therapy session corresponding to the selected node and present the additional information. Moreover, nodes 206 may comprise summarized representations of the therapy session information for corresponding therapy sessions that include an abstraction of therapy session information for the therapy sessions.

In one example, user interface 120 may present a screen similar to that illustrated by FIG. 9 for the corresponding therapy session, to depict an infusion pattern for the corresponding therapy session, an amount of therapeutic agent administered at each step during the infusion pattern, a comparison to a historical infusion pattern, or other information. As another example, user interface 120 may present a screen similar to that illustrated by FIG. 8 to represent information regarding the therapeutic agent administered during the corresponding therapy session. Other additional information may also be displayed via a textual and/or graphical representation, or a combination thereof.

In the example of FIG. 10, graph 200 indicates that, over time, IMD 12 has been gradually programmed in successive programming sessions to administer greater amounts of a therapeutic agent. Although a programming session preceding therapy session 202D resulted in a reduction in the amount of therapeutic agent delivered to the patient other programming sessions successively resulted in delivery of incrementally greater amounts of therapy agent. Graph 200 also indicates that IMD 12 is programmed to administer 9.8 mg/day of the therapeutic agent for a most recent therapy session, represented as "today."

Using the therapy session information presented by programmer 20, a clinician may determine whether to reprogram IMD 12 to deliver more or less of the therapeutic agent, or determine that the current programming is sufficient. In this manner, the clinician may readily observe changes to the average daily dose or programmed daily dose of therapeutic agent administered to the patient over several historical therapy sessions, which may assist the clinician in performing titration. In some examples, when the therapeutic agent is a well known drug with well defined titration bounds (e.g., maximum and/or minimum therapeutic agent amounts to be delivered to the patient), user interface 120 may further display the bounds for a pending dosing program of an upcoming therapy session to assist a user in programming IMD 12.

Figure 11:
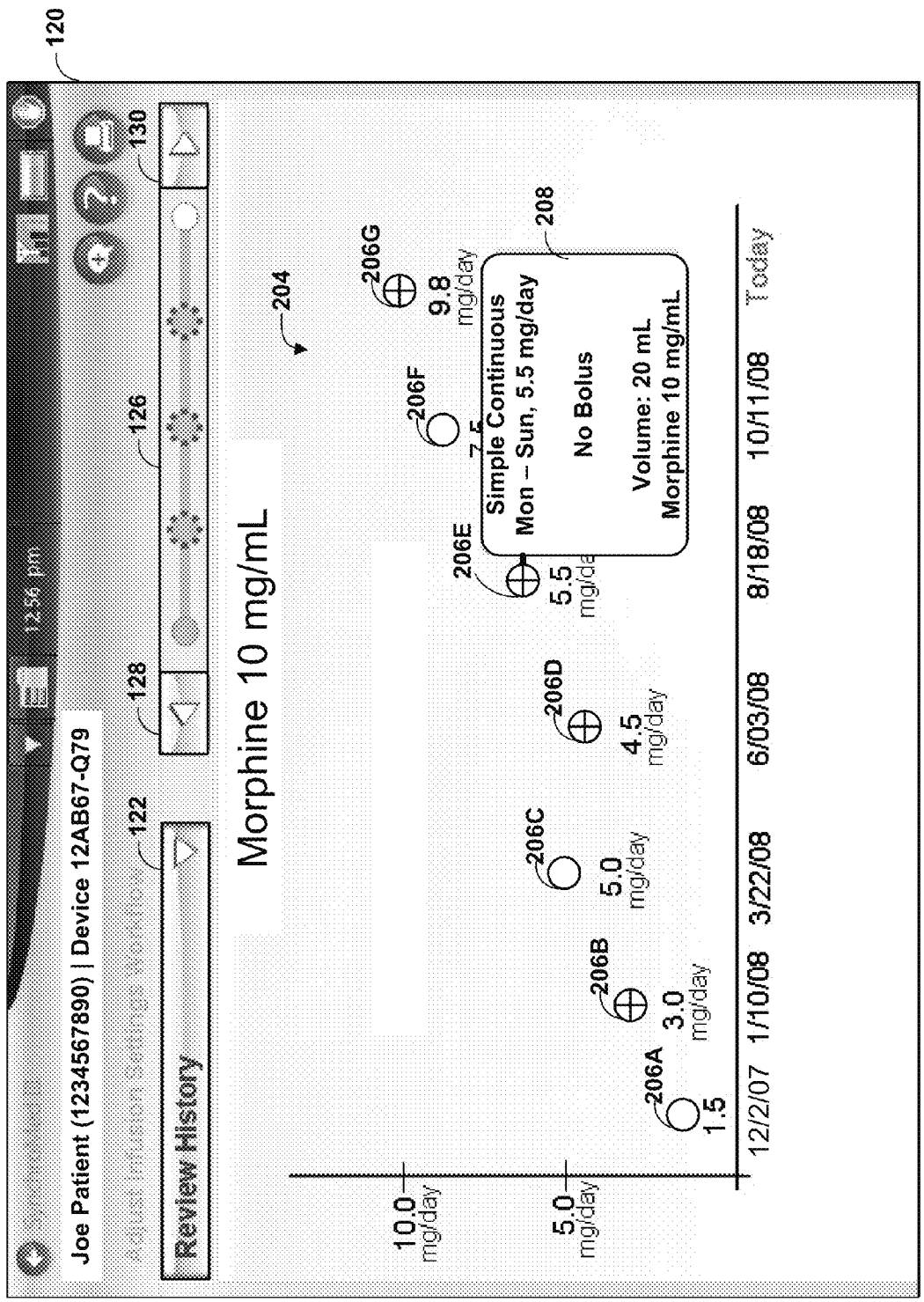
FIG. 11 is a screenshot illustrating an example user interface for displaying a graphical trend of session history information that includes session details.

FIG. 11 is a screenshot illustrating an example user interface for displaying a graphical trend of session history information that includes details of dosing program in addition to trend information. In one example, processor 52 of programmer 20 may cause user interface 120 to display graph 204 when a user selects "Review history" from drop-down menu 122. Graph 204 includes nodes 206A-206G (nodes 206) that each represents information regarding a corresponding therapy session. Nodes 206 may represent information that is similar to nodes 202 of FIG. 10. However, some of nodes 206 may include additional information in the form of clinician annotations.

In the example of FIG. 11, nodes 206B, 206D, 206E, and 206G include a cross or plus sign, representing that extra details regarding the dosing program are available for these nodes. In other examples, user interface 120 may display other indications of a dosing program detail for one of nodes 206, such as using different colors, shading, hatching, outlining, other symbols, highlighting, flashing, varying sizes of nodes 206, or other methods for indicating that one of nodes 206 includes additional details. A user may select one of nodes 206B, 206D, 206E, and 206G by, for example, moving a pointer (e.g., with a mouse or other user interface device) over a desired one of nodes 206B, 206D, 206E, and 206G and pressing a button, such as a mouse button. Other selection methods may also be used, such as by touching one of nodes 206B, 206D, 206E, and 206G when user interface 120 comprises a touch screen, e.g., with a finger or a stylus. In some examples, a user may select one of nodes 206B, 206D, 206E, and 206G by "hovering over" the representation of the node with a mouse cursor. That is, the user may position a cursor over one of nodes 206B, 206D, 206E, and 206G and then not move the cursor for a certain period of time, which processor 52 may interpret as a selection of the corresponding one of nodes 206B, 206D, 206E, and 206G.

In some examples, programmer 20 may retrieve data regarding sensed diagnostic conditions from IMD 12. For example, programmer 20 may retrieve data regarding one or more of the integrity of the catheter (patency, blockage, kinking, or other conditions preventing flow to the tip), the status of the pumping mechanism (missing or extra infusion based on stalls or other mechanical conditions), and the status of the reservoir (over or under pressure conditions). Programmer 20 may further retrieve data regarding clinical action sensed by IMD 12, such as insertion of a needle in one of the ports for purposes of refill or catheter access, reservoir filling or aspiration, and catheter connection or disconnection as in a revision surgery or replacement. Programmer 20 may also retrieve data regarding a downloaded program revision to IMD 12. That is, IMD 12 may have received a programming revision during a therapy session that modified programming of IMD 12 for that therapy session. Programmer 20 may therefore retrieve data that indicates that this programming revision occurred.

User interface 120 may display one or more representations of the retrieved data using a symbol similar to, but different than, the example symbol of FIG. 11. For example, user interface 120 may display an exclamation point next to one of nodes 206 for which there exists data regarding a sensed diagnostic event. Other methods as described above for depicting the presence of an annotation may also be used to represent the presence of data regarding a sensed diagnostic event for a particular therapy session corresponding to one of nodes 206. A user may select one of these nodes for which there exists sensed diagnostic event data, and user interface 120 may display a detailed representation of the sensed diagnostic event, e.g., "catheter length revision detected," or "pump malfunction detected." Inclusion of such detected diagnostic conditions or clinical actions in a displayed representation of a therapy session of a session history may improve interpretation of such histories. In this manner, user interface 120 may include a representation that a programmed pump priming activity occurred where no catheter aspiration was detected, which may help a user viewing user interface 120 to explain unexpected patient symptoms or non-optimal therapy outcomes.

Likewise, user interface 120 may also display a representation that a one-time event occurred for a particular therapy session corresponding to one of nodes 206, e.g., using a symbol or other methods as described in this disclosure. The one-time event may comprise, for example, one or more of a priming procedure, a bridging procedure, a therapeutic bolus, a catheter length revision, or other one-time event for IMD 12. In some examples, programmer 20 may retrieve data regarding the one-time event(s) from IMD 12. IMD 12 may store data regarding the one-time event(s) in memory 40.

Upon selecting one of nodes 206B, 206D, 206E, and 206G, user interface 120 displays all or a portion of the session history's dosing program associated with the selected node. In the example of FIG. 11, user interface 120 displays dosing program detail 208, related to the therapy session represented by node 206E. Dosing program detail 208 may be presented as a pop-up or drop-down window that, in effect, expands the node 206 to provide access to additional information. In the example of FIG. 11, dosing program detail 208 represents that the dosing program of the therapy session corresponding to node 206E includes a simple continuous infusion pattern every day of the week (i.e., Monday through Sunday), and delivers 5.5 mg/day.

In this manner, a user may select a node and user interface 120 may extract additional information for the selected node and present the additional information to the user. Likewise, user interface 120 may represent a summary or an abstraction of the available information for each therapy session in the form of nodes 206. That is, each of nodes 206 may represent only a subset of all of the available information for a corresponding therapy session. In this manner, nodes 206 may comprise a representation of the therapy sessions, and the representation may comprise an abstraction of therapy session information for the therapy sessions. As an illustration, although a therapy session may be characterized by a variety of different data, the therapy session could be summarized or abstracted, for purposes of presentation to a user, by presenting only an average daily dosage for a therapy session.

Figure 12:
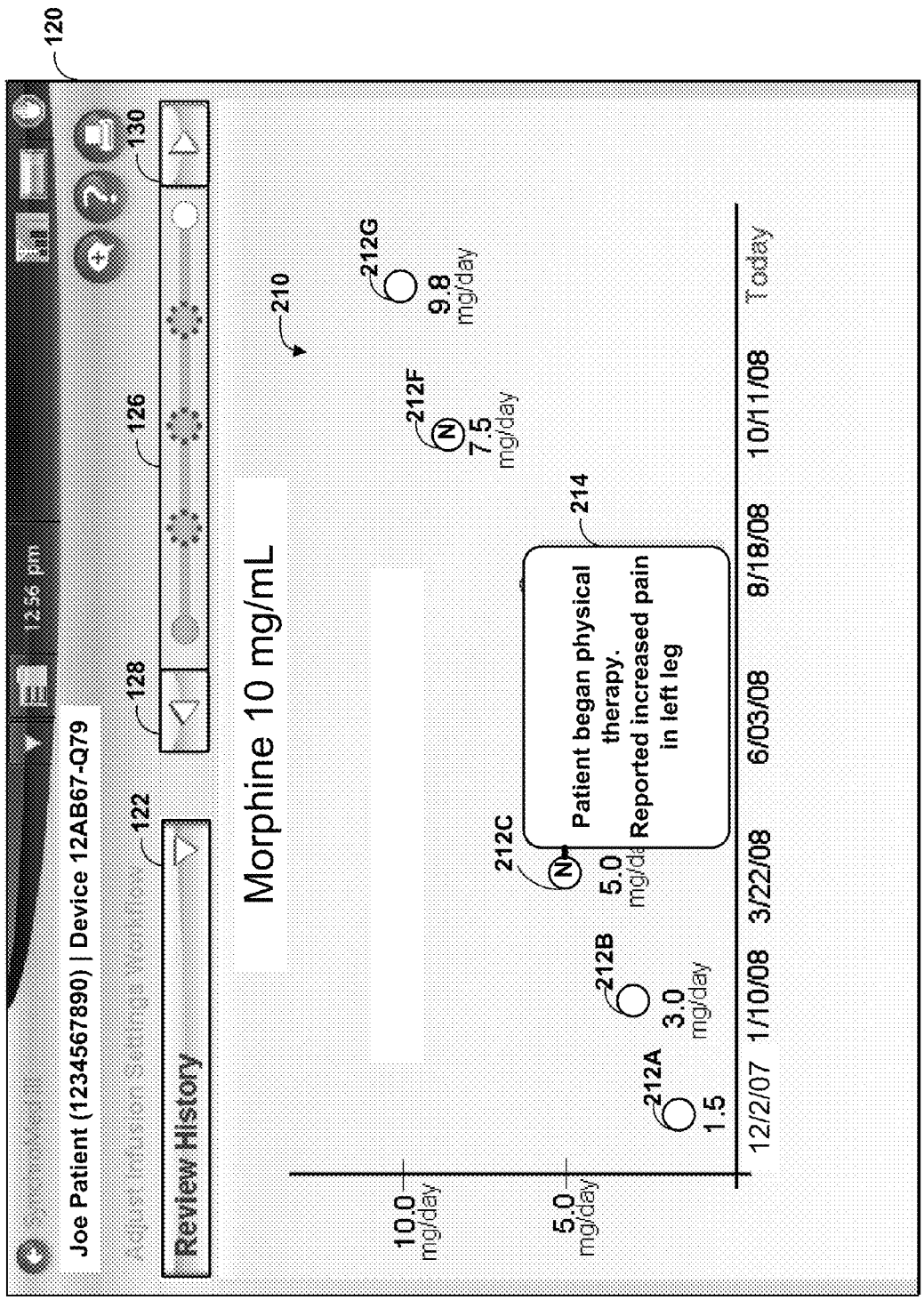
FIG. 12 is a screenshot illustrating an example user interface for displaying a graphical trend of session history information that includes clinician annotations, patient feedback, and comments.

FIG. 12 is a screenshot illustrating another example user interface for displaying a graphical trend of session history information that includes clinician annotations and patient feedback and comments. In one example, processor 52 may cause user interface 120 to display graph 210 when a user selects "Review history" from drop-down menu 122. Graph 210 includes nodes 212A-212G (nodes 212) that each represent a summary of information regarding a corresponding therapy session. Nodes 212 may represent information that is similar to nodes 202 of FIG. 10. However, some nodes 212 may include additional information in the form of patient annotations, which may include information entries made by patients concerning particular therapy sessions. Clinician annotations may include information entries made by a clinician with respect to particular therapy sessions. The information entries may be text entries or other information provided by the clinician, e.g., by checking boxes, selecting values, uploading data, or the like.

In the example of FIG. 12, nodes 212C and 212F include the letter "N" to indicate that nodes 212C and 212F include annotations. In other examples, user interface 120 may display other indications of a clinician annotation for one of nodes 212, such as using different colors, shading, hatching, outlining, other symbols, highlighting, flashing, varying sizes of nodes 212, or other methods for indicating that one of nodes 206 includes an annotation. A user may select an annotated one of nodes 212 using any of the example methods discussed with respect to nodes 206 of FIG. 11, or other similar methods.

In some cases, clinician annotations may include date information to indicate dates associated with different clinician entries or comments. In many cases, however, clinician annotations may be entered during a single clinic visit, and may have the same date for a given therapy session. Clinician annotation 214 also may represent that there were no supplemental boluses administered during the therapy session. Clinician annotation 214 may also represent a total volume of fluid at the beginning of the therapy session, and a quantity of therapeutic agent in the fluid, for example, 10 mg/mL of morphine as the therapeutic agent. Hence, a clinician annotation may describe the type of dosing program (e.g., simple continuous), the dosage volume, the dosage concentration, the type of drug, and the existence of any supplemental boluses.

Upon selecting nodes 212C or 212F, user interface 120 displays an annotation for the selected one of nodes 212. In the example of FIG. 12, user interface 120 displays patient annotation 214. An annotation may include information reported by a patient or by a clinician or other user, such as information relating to perceived efficacy, daily activities, oral medication changes, or general health or quality of life. The example patient annotation 214 informs a user that the patient began physical therapy during the therapy session associated with node 212C. Patient annotation 214 also informs the user that the patient reported increased pain in the patient's left leg.

A user may use this information to assist in determining whether the reported increase in pain was a result of the amount of therapeutic agent delivered to the patient, a result of the physical therapy, or due to some other cause. In this manner, the user may use the information of graph 210 to assist in deciding whether and how to modify physical therapy, whether and how to modify programming of IMD 12, or other characteristics of the patient's therapy. In this manner, a user may select a node and user interface 120 may extract additional information for the selected node and present the additional information to the user.

A therapy session may extend for several days or weeks, and the patient may submit patient annotations on different dates during a therapy sessions. For this reason, in some cases, the patient annotations may include date information to indicate dates associated with different patient entries or comments. Also, in some examples, patient feedback may include subjective patient feedback, where the patient quantifies a particular symptom. In other examples, patient feedback may include objective measures, such as muscle tone, an activity metric (representative of how active the patient was during the therapy session), range of motion of a joint or appendage, or other objective indications. In some examples, patient feedback may include a correlation with oral medication used to supplement therapy administered by IMD 12.

Figure 13:
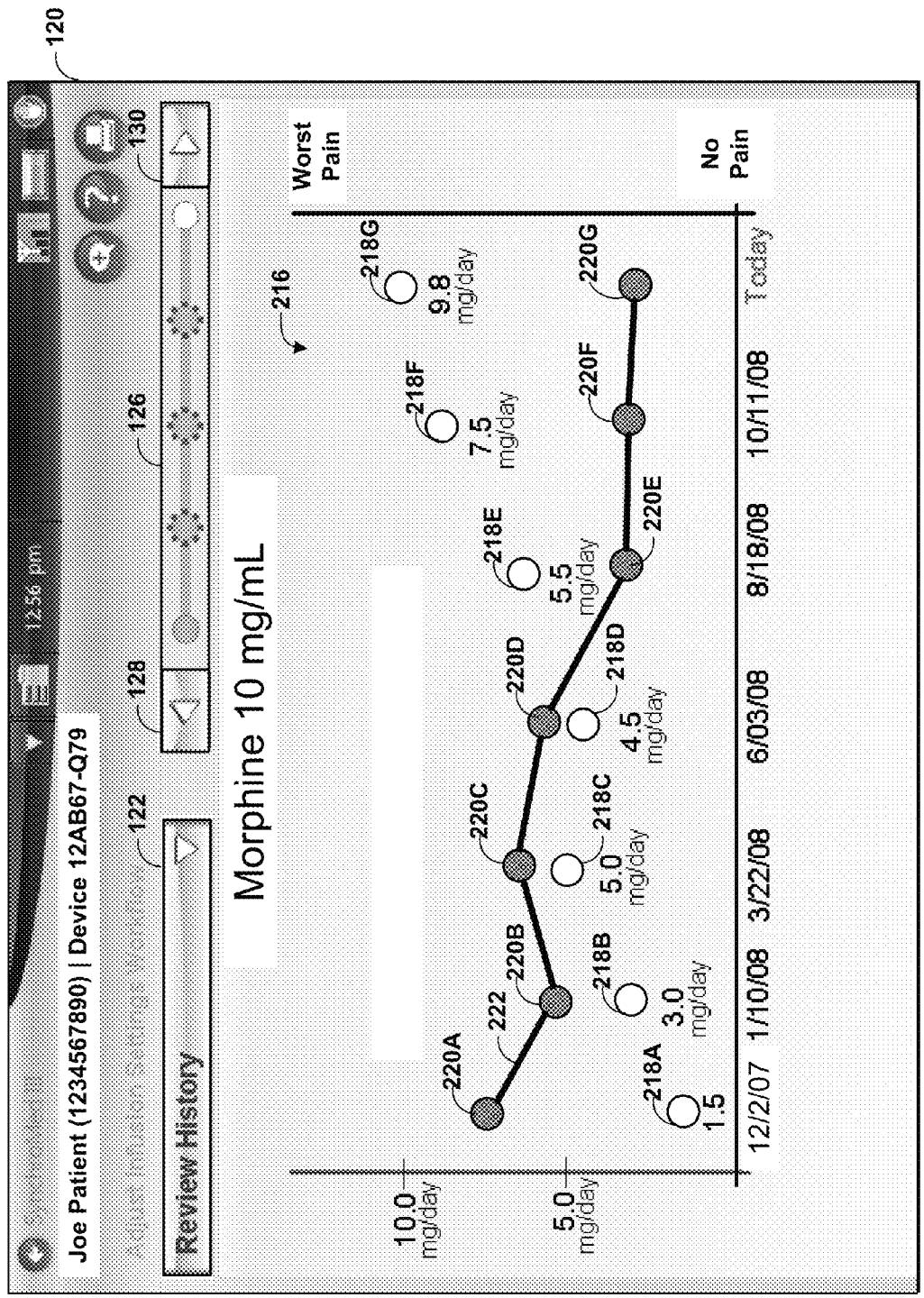
FIG. 13 is a screenshot illustrating an example user interface for displaying a graphical trend of session history information that includes a second graphical trend corresponding to patient feedback related to the outcome of the therapy.

FIG. 13 is a screenshot illustrating an example user interface for displaying a graphical trend of session history information that includes a second graphical trend corresponding to patient feedback related to the outcome of the therapy. In one example, processor 52 may cause user interface 120 to display graph 216 when a user selects "Review history" from drop-down menu 122. Graph 216 includes nodes 218A-218G (nodes 218) that each represent information regarding a corresponding therapy session. Nodes 218 may represent information that is similar to nodes 202 of FIG. 10.

In addition, graph 216 includes nodes 220A-220G (nodes 220) along a trend line 222 that interconnects the nodes. Nodes 220 generally correspond to reported pain levels by patient 16 during the therapy session. Pain level information may be reported by the patient to a clinician during a clinic visit for a programming session, or entered into a patient programmer. In the example of FIG. 13, each one of nodes 220 corresponds to a pain level experienced by the patient during a corresponding therapy session represented by nodes 218. For example, node 220A corresponds to a pain level reported by the patient during the therapy session corresponding to node 218A. In other examples, nodes 220 may correspond to other symptoms or reports, e.g., tiredness, muscle tone, spasticity measure, functional outcome, number of episodes of a symptomatic event (incontinence, seizures, etc.), or other symptoms or reports. Each of nodes 220 relates to a scale on the right side of graph 216, where higher on the y-axis represents greater pain and lower on the y-axis represents less pain.

A user may observe information from graph 216 to readily observe correlations between pain experienced by the patient and indicated by nodes 220 for different therapy sessions and the amount of a therapeutic agent administered to the patient and indicated by nodes 218 for different therapy sessions. In the example of FIG. 13, as a higher average daily dose of the therapeutic agent is administered to the patient, the patient has reported less pain. The user may therefore use the information of graph 216 to assist in determining whether and how to modify future therapy sessions and programming of IMD 12. Hence, in the example of FIG. 13, trends in patient condition for historical therapy sessions may be presented with trends in dosing program changes over the same historical therapy sessions.

Other patient information in addition, or as an alternative, to patient pain may be presented as patient information for correlation with therapy information. Examples of other patient information include patient activated bolus counts, oral medications, patient work or leisure events, or the like. Likewise, other therapy information may be presented, such as type of dosing pattern, therapy revisions such as catheter or pump revision, drug changes, drug concentration changes, or the like.

Figure 14:
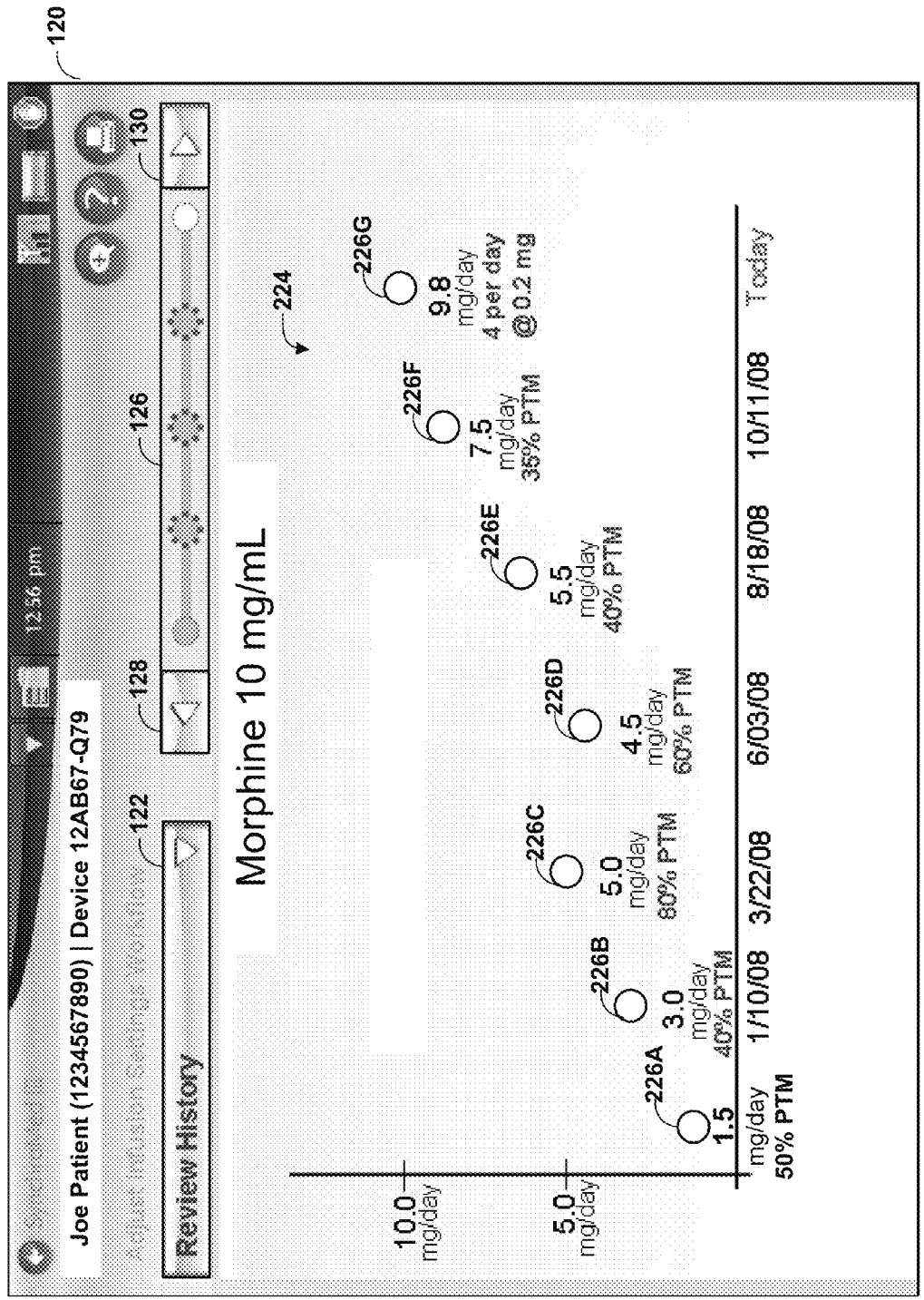
FIG. 14 is a screenshot illustrating an example user interface for displaying a graphical trend of session history information that includes indications of supplemental bolus requests by the patient.

FIG. 14 is a screenshot illustrating an example user interface for displaying a graphical trend of session history information that includes indications of supplemental bolus requests by the patient. A patient may be given a patient programmer device to, for example, request supplemental boluses of the therapeutic agent, i.e., as supplemental boluses to dosing delivered according to a dosing program. The patient programmer device may comprise, for example, a personal therapy manager (PTM) available from Medtronic for controlling SynchroMed® drug pumps or other implantable medical devices. The patient programmer device may be programmed to cause IMD 12 to deliver a supplemental bolus in response to a patient's request for a supplemental bolus. The patient programmer device may further be programmed to only permit a limited number of supplemental boluses in a certain period of time, or to impose a lockout period to require a minimum period of time between successive supplemental boluses.

In one example, processor 52 may cause user interface 120 to display graph 224 when a user selects "Review history" from drop-down menu 122. Graph 224 includes nodes 226A-226G (nodes 226) that each represents information regarding a corresponding therapy session. Nodes 226 may represent information that is similar to nodes 202 of FIG. 10. In addition, user interface 120 may present a textual or graphical representation of supplemental bolus information. In the example of FIG. 14, user interface 120 presents a textual representation of supplemental bolus information below each of nodes 226. In this example, the textual display includes a numeric percentage.

In one example, user interface 120 presents the numeric percentage as a representation of a percentage of the average daily dose that was requested by the patient as supplemental boluses, as opposed to programmed average daily doses. For example, node 226B represents that 3.0 mg/day were delivered on average to patient 12, and 40% of the 3.0 mg/day were supplemental boluses requested by the patient. A user may use this information to determine whether the programmed daily dose should be increased for the patient, e.g., when the patient on average requests more than the programmed dose each day.

In other examples, user interface 120 may present the percentage information in other textual or graphical ways, such as, for example, using pie charts, bar charts, or other methods. For example, user interface 120 may present each of nodes 226 as individual pie charts, where a first portion of each pie chart represents a programmed daily dose and a second portion of each pie chart represents a dose according to patient-requested supplemental boluses for the corresponding therapy session. The pie chart may include different colors, shading, hatching, outlining, or other indications of the first and second portions thereof.

In some examples, user interface 120 may present additional information as to a time of day at which the patient requested supplemental boluses. A user may also reprogram IMD 12 according to the requests for supplemental boluses such that IMD 12 automatically delivers an extra dose of the therapeutic agent at a commonly requested time, e.g., if the user notices that the patient commonly requests supplemental boluses at the same time each day.

In another example, the numeric percentage may represent a percent of requested supplemental boluses that were actually granted. A user may then determine whether the limit on the number of supplemental doses is effective, whether alternative therapies or therapeutic agents would be more appropriate for the patient, or other information. Also, in some cases, an excessive number of ungranted requests may indicate other patient issues to be addressed by a clinician, such as trends toward over-dependence on therapeutic agent delivered by the implantable drug pump. Alternatively, an absolute measure may be included instead of a percentage, such as average bolus activations per day during the session.

Figure 15:
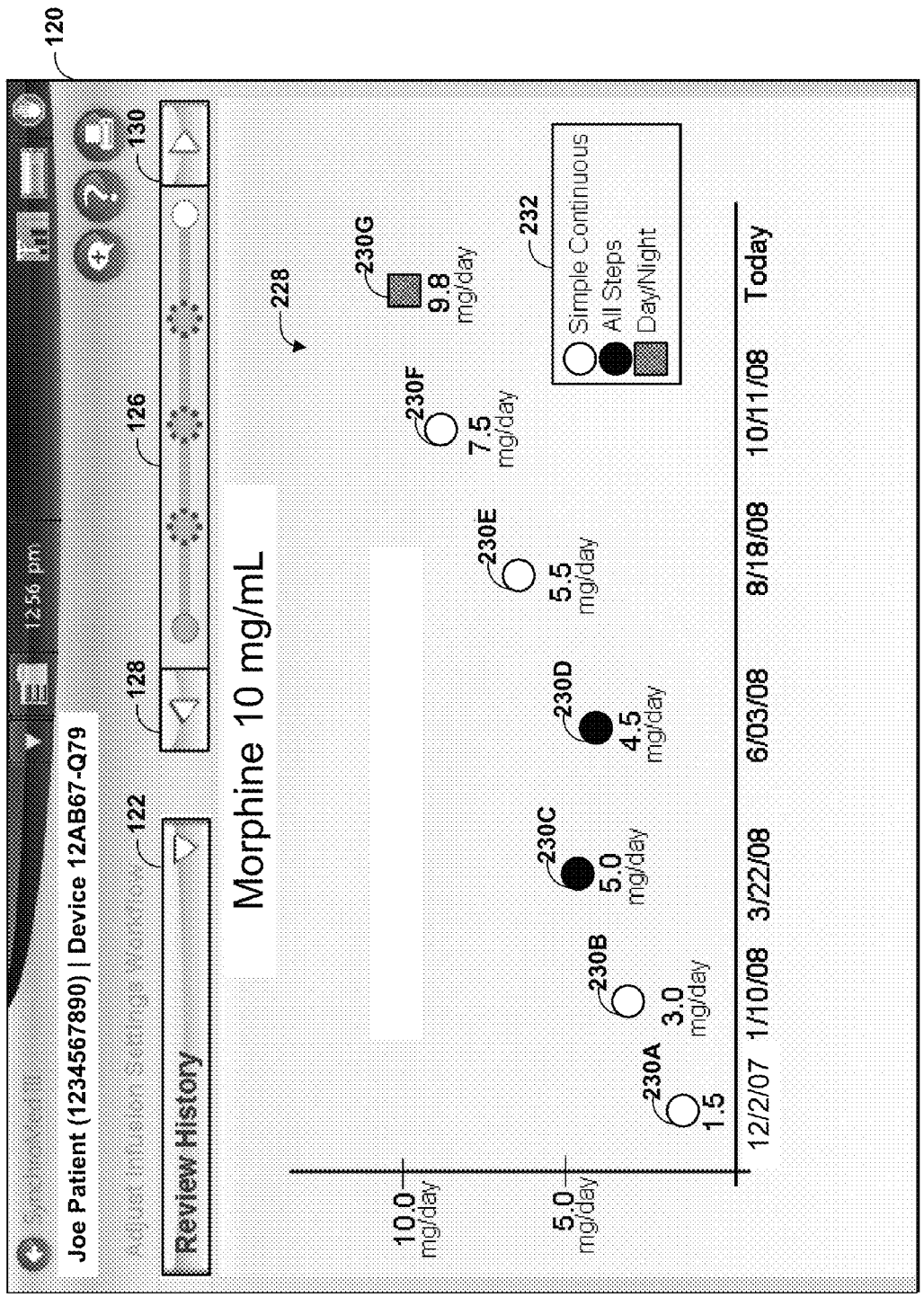
FIG. 15 is a screenshot illustrating an example user interface for displaying a graphical trend of session history information in which nodes of the trend represent infusion patterns for each therapy session.

FIG. 15 is a screenshot illustrating an example user interface for displaying a graphical trend of session history information in which nodes of the trend represent infusion patterns for each therapy session. In one example, processor 52 may cause user interface 120 to display graph 228 when a user selects "Review history" from drop-down menu 122. Graph 228 includes nodes 230A-230G (nodes 230) that each represents information regarding a corresponding therapy session. Nodes 230 may represent information that is similar to nodes 202 of FIG. 10.

In addition, each of nodes 230 represents an infusion pattern for the corresponding therapy session. In the example of FIG. 15, the infusion patterns represented include a simple continuous infusion pattern (i.e., a constant rate of fluid delivery continuously applied throughout the duration of the therapy session), an "all steps" infusion pattern (in which a clinician may define one or more "steps," each corresponding to a rate at which to deliver fluid and a duration of time over which to deliver the fluid at that rate), and a day/night infusion pattern, in which IMD 12 delivers fluid at a first rate during the day and at a second rate during the night.

User interface 120 displays key 232, which indicates that white circular nodes correspond to the simple continuous infusion pattern, black circular nodes correspond to the all steps infusion pattern, and gray squares correspond to the day/night infusion pattern. In the example of FIG. 15, nodes 230A, 23B, 230E, and 230F correspond to the simple continuous pattern, nodes 230C and 230D correspond to the all steps infusion pattern, and node 230G corresponds to the day/night infusion pattern. In other examples, other methods may be used to represent various infusion patterns, such as different colors, shading, hatching, outlining, displaying a symbol within the node, highlighting, flashing, varying sizes of nodes 206, or other methods. In this manner, nodes 206 may comprise an abstraction of therapy session information.

Figure 16:
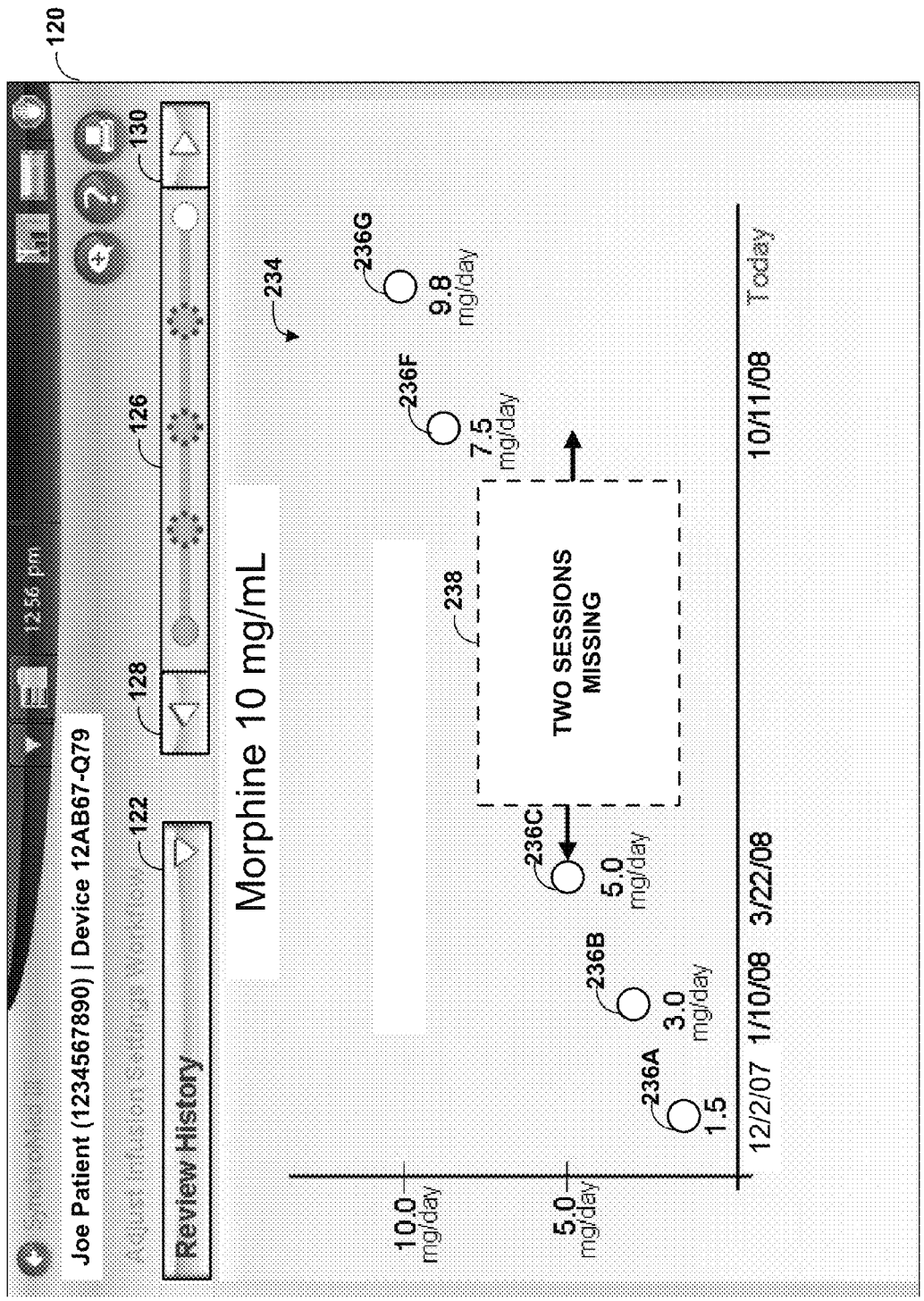
FIG. 16 is a screenshot illustrating an example user interface for displaying a graphical trend of session history information that further indicates that information for certain therapy sessions is missing.

FIG. 16 is a screenshot illustrating an example user interface for displaying a graphical trend of session history information that further indicates that information for certain therapy sessions is missing. Sessions may be missing if there are memory limitations in an implant, if different programmers are used for programming sessions, or if the data cannot be accessed due to connection issues or other networking problems. In one example, processor 52 may cause user interface 120 to display graph 234 when a user selects "Review history" from drop-down menu 122. Graph 234 includes nodes 236A-236G (nodes 236) that each represents information regarding a corresponding therapy session. Nodes 236 represent certain information that is similar to nodes 202 of FIG. 10. However, in the example of FIG. 16, there are no nodes displayed in graph 234 corresponding to nodes 202D, 202E of FIG. 10, as these nodes are missing.

In some examples, a new programmer may communicate with an existing IMD, or an existing programmer may communicate with a new IMD. In any case, there may arise situations in which data is not readily available to the programmer or other device that is displaying graph 234. When data is unavailable, e.g., stored in a different location, lost, corrupted, or otherwise not readily available, user interface 120 may display a representation that certain data is missing. Processor 52 may determine that data is missing by calculating intervals between therapy sessions. For example, a user may establish a configuration that an IMD is to be reprogrammed periodically, e.g., once every month, once every two months, once per quarter, or other period of time.

When processor 52 determines that no data is available for a period of time during which data should be available, processor 52 may cause user interface 120 to display a representation that certain data is missing. In the example of FIG. 16, user interface 120 displays dialog box 238 that indicates that data for two therapy sessions is currently missing. A user may then attempt to determine whether the data is stored in another location, e.g., on another programmer or another IMD. The user may also be alerted that the data is missing, and therefore avoid making an incorrect decision. For example, the user may be put on notice that the data is missing, and therefore avoid concluding that there simply were no additional therapy sessions during the corresponding time period, or that a particular therapy session was exceptionally long (e.g., the therapy session corresponding to node 236F).

Figure 17:
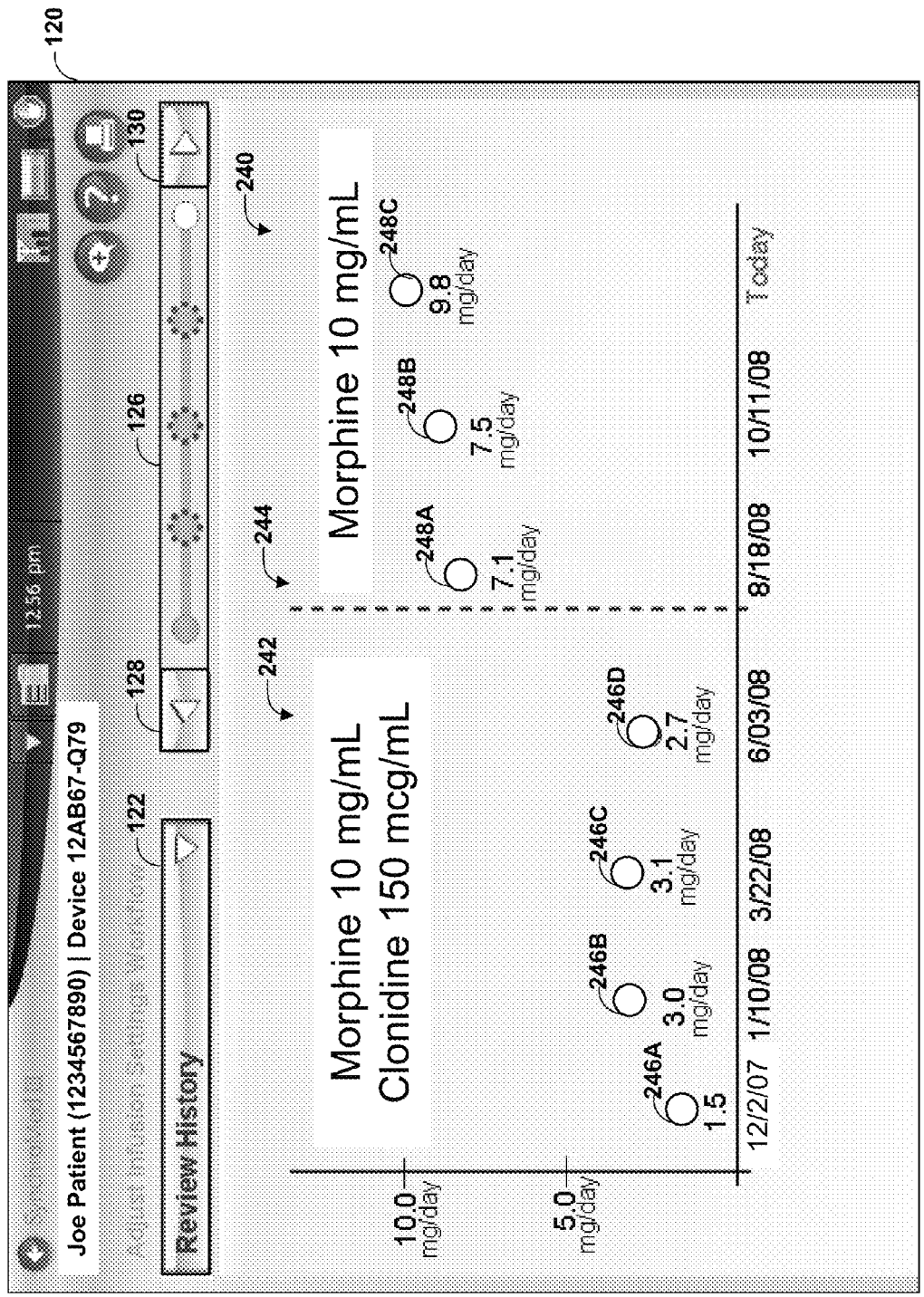
FIG. 17 is a screenshot illustrating an example user interface for displaying a graphical trend of session history information that indicates that a change in fluids has occurred.

FIG. 17 is a screenshot illustrating an example user interface for displaying a graphical trend of session history information that indicates that a change in fluids has occurred. In one example, processor 52 may cause user interface 120 to display graph 240 when a user selects "Review history" from drop-down menu 122. Graph 240 includes nodes 246A-246D (nodes 246) and nodes 248A-248C (nodes 248), each of which represents information regarding a corresponding therapy session.

Nodes 246 correspond to therapy sessions using a fluid containing morphine at 20 mg/mL and clonidine at 150 mcg/mL. Nodes 246 are presented as sub-graph 242. Nodes 248 correspond to therapy sessions using a fluid containing morphine at 10 mg/mL. Nodes 248 are presented as sub-graph 244. A user may observe, from the information presented by graph 240, that a lower overall amount of therapeutic agent was administered to the patient during therapy sessions corresponding to sub-graph 242, and that a greater amount of therapeutic agent was administered to the patient during therapy sessions corresponding to sub-graph 244. In this manner, user interface 120 may simultaneously represent information regarding a first set of therapy sessions during which a first therapeutic agent was administered and a second set of therapy sessions during which a second therapeutic agent was administered. Likewise, the representation comprises temporally-ordered representations of the first and second sets of therapy sessions.

Figure 18:
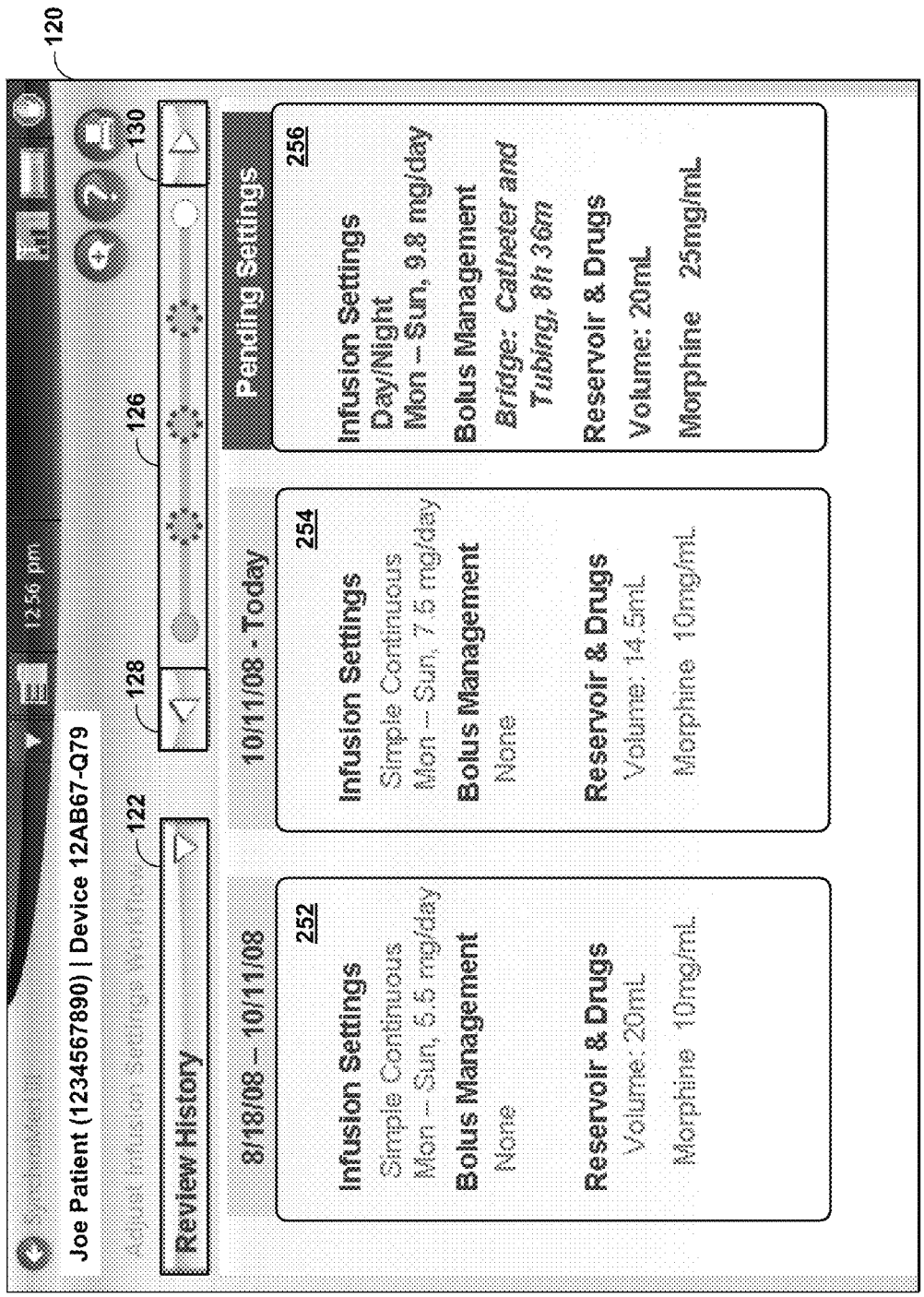
FIG. 18 is a screenshot illustrating an example user interface for displaying a textual representation of session history information.

FIG. 18 is a screenshot illustrating an example user interface for displaying a textual representation of session history information. In the example of FIG. 18, user interface 120 displays textual representations 252, 254, 256, each corresponding to different therapy sessions. Textual representation 252 corresponds to a therapy session administered between Aug. 18, 2008 and Oct. 11, 2008, in which IMD 12 was programmed to deliver fluid at a simple continuous rate such that 5.5 mg of therapeutic agent were administered to patient 16 per day.

Textual representation 254 corresponds to a therapy session administered between Oct. 11, 2008 and "today," i.e., the day on which the current programming session is occurring, in which IMD 12 was programmed to deliver fluid at a simple continuous rate such that 7.5 mg of therapeutic agent were administered to patient 16 per day. Textual representation 256 corresponds to pending settings for IMD 12 in which IMD 12 will administer fluid according to a day/night infusion pattern such that 9.8 mg of therapeutic are administered to patient 16 per day.

The pending settings may be new programming settings being considered by a clinician for delivery in the next therapy sessions. Changes from current settings, or between one session history and another, may be highlighted via color or font change to emphasize differences over time. Textual representation 256 additionally represents that a bridging phase will be performed on the catheter and tubing of IMD 12 because the fluid has changed from 10 mg/mL of morphine to 25 mg/mL of morphine.

Figure 19:
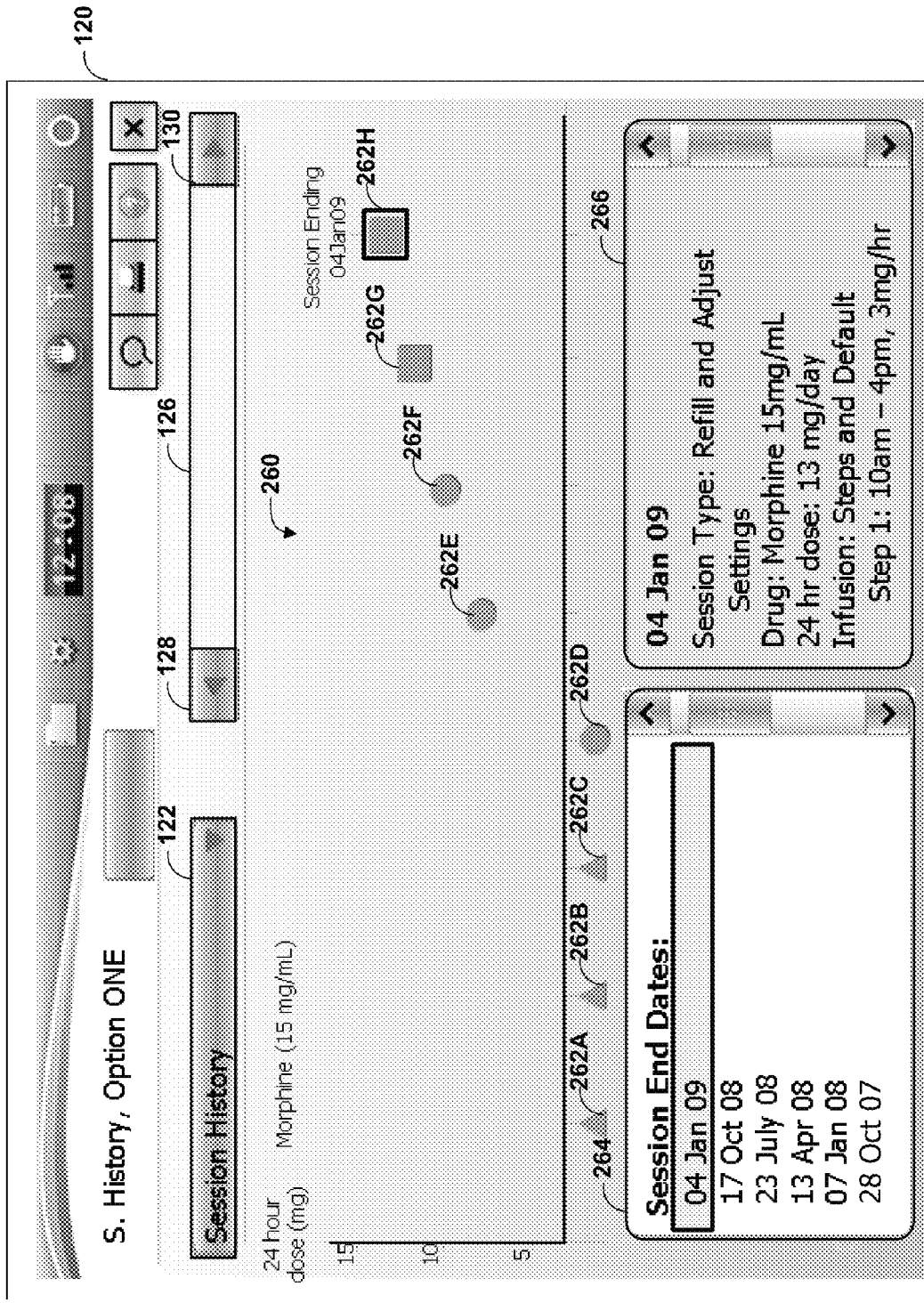
FIG. 19 is a screenshot illustrating an example user interface for displaying a graphical trend of session history information in which nodes represent an infusion pattern for the therapy session.

FIG. 19 is a screenshot illustrating an example user interface for displaying a graphical trend of session history information in which nodes represent an infusion pattern for the therapy session. In one example, processor 52 may cause user interface 120 to display graph 260 when a user selects "Session history" from drop-down menu 122. "Session history" may be an option of drop-down menu 122 in addition or alternative to "Review history" as discussed with respect to the examples of FIGS. 10-18. Graph 260 includes nodes 262A-262D (nodes 262), each of which represents information regarding a corresponding therapy session. User interface 120 also displays textual session information in text box 266 and corresponding dates in text box 264.

A user may select a therapy session either by selecting one of nodes 262 or by selecting a session end date from text box 264. In the example of FIG. 19, a user has selected the therapy session corresponding to node 262H. When a user selects one of nodes 262, user interface 120 highlights the selected node and the corresponding date in text box 264. Similarly, when a user selects one of the dates in text box 264, user interface 120 highlights the selected date and the corresponding one of nodes 262. Thus, in the example of FIG. 19, user interface 120 has highlighted node 262H and "4 Jan. 2009" date in text box 264.

When a user selects one of nodes 262 or one of the dates of text box 264, user interface 120 retrieves and displays textual information about the corresponding therapy session in text box 266. In the example of FIG. 19, text box 266 displays textual information related to the therapy session ending Jan. 4, 2009, represented by node 262H. Text box 266 may include information related to a programming session for the therapy session (that the programming session included refilling and adjusting settings of IMD 12), a therapeutic agent used during the therapy session (morphine at 15 mg/mL in this example), a total amount of therapeutic agent administered during the therapy session (13 mg/mL in this example), and infusion information, such as each step of each therapy schedule of the dosing program for the therapy session.

Also in the example of FIG. 19, nodes 262A-262D are displayed below the x-axis of graph 260. User interface 120 may display nodes below the x-axis when therapy sessions corresponding to those nodes utilized a different therapeutic agent than the therapeutic agent of the nodes that are displayed above the x-axis. The difference in therapeutic agents may comprise a different combination of therapeutic agents or a different individual therapeutic agent. For example, text box 266 represents that the therapeutic agent for the therapy session corresponding to node 262H was morphine. Therefore, therapy sessions corresponding to each of nodes 262E-262H utilized morphine as the therapeutic agent, and the therapy sessions corresponding to nodes 262A-262D utilized a therapeutic agent other than morphine. In this manner, user interface 120 may present a summarized representation of therapy sessions with the same therapeutic agent and with different therapeutic agents.

As discussed above, a user has selected node 262H in the example of FIG. 19. Therefore, user interface 120 displays node 262H above the x-axis and any of nodes 262 that correspond to therapy sessions for which a therapeutic agent was the same as the therapeutic agent of the therapy session corresponding to node 262H, and the remaining nodes 262 below the x-axis. When a user selects one of nodes 262A-262D, user interface 120 may display nodes 262E-262H below the x-axis and any of nodes 262A-262D that correspond to therapy sessions for which the therapeutic agent was the same as the therapeutic agent of the therapy session corresponding to the selected node above the x-axis.

In some examples, programmer 20 may not have access to enough information to display a full graphical trend for each therapy session. Therefore, user interface 120 may represent therapy sessions for which average dose information or therapeutic agent information is unknown, but for which some therapy session information exists, as nodes below the x-axis, as shown in the example of FIG. 19.

In the example of FIG. 19, nodes 262 are each of a plurality of different shapes. User interface 120 may represent various information using different shapes for nodes 262. For example, the shapes may correspond to various infusion patterns or dosing programs for a corresponding therapy session. For example, square nodes (nodes 262G and 262H) may correspond to all steps infusion patterns, circular nodes (nodes 262D, 262E, 262F) may correspond to day/night infusion patterns, and triangular nodes (nodes 262A, 262B, 262C) may correspond to simple continuous infusion patterns.

Figure 20:
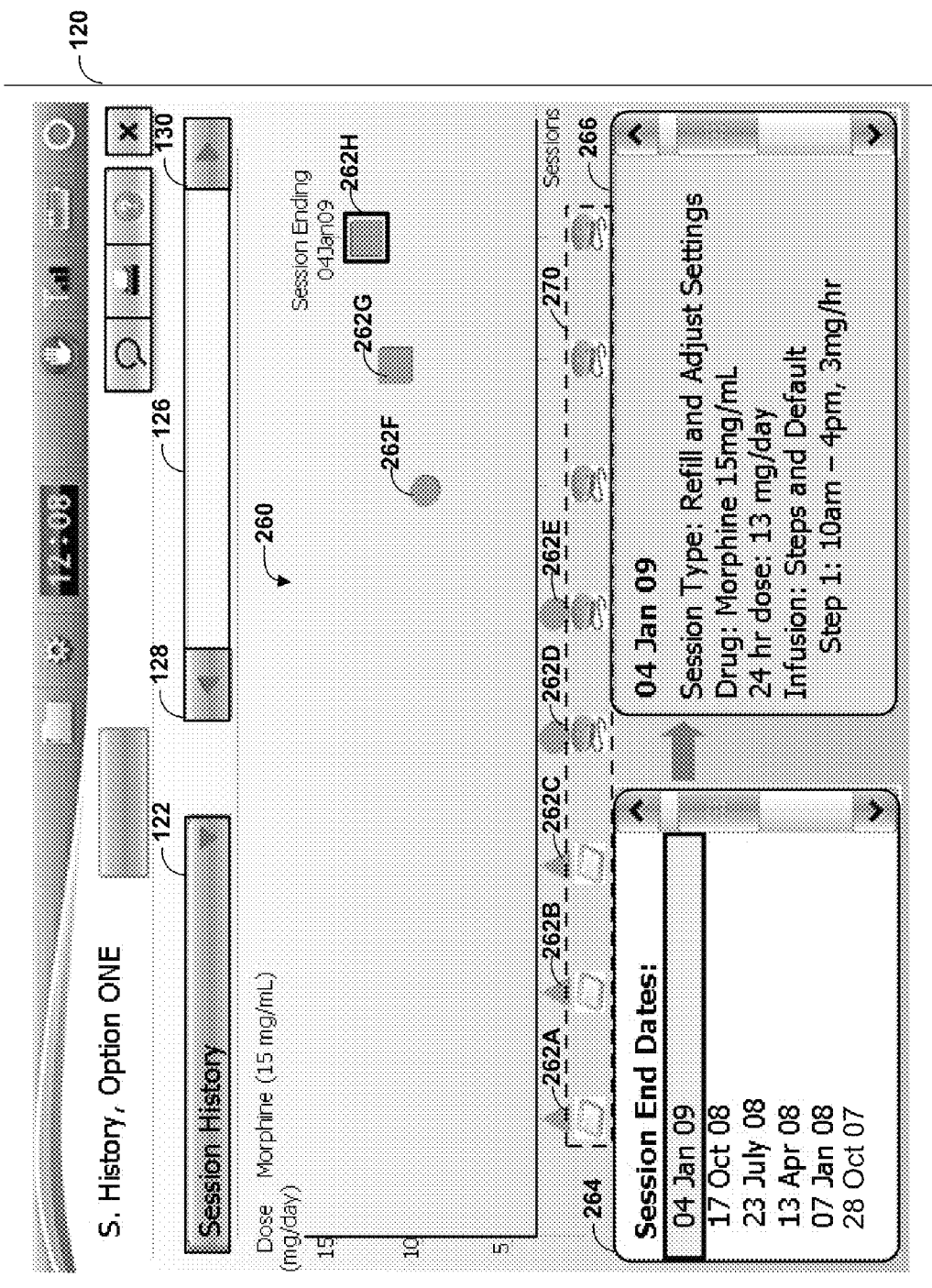
FIG. 20 is a screenshot illustrating an example user interface for displaying a graphical trend of session history information that also graphically represents a storage location of the session history information.

FIG. 20 is a screenshot illustrating an example user interface for displaying a graphical trend of session history information that also graphically represents a storage location of the session history information. As in the example of FIG. 19, user interface 120 displays graph 260 that includes nodes 262, as well as text boxes 264, 266. In addition, user interface 120 displays icons 270 that represent a data storage location for data relating to therapy session information. That is, icons 270 represent where data for each therapy session is stored. In some examples, in which a first IMD is replaced by a second IMD, it may be necessary to accomplish data integration from multiple sources.

Processor 52 may distinguish between different IMDs or programmers by referencing a device serial number with a unique session counter. Processor 52 may maintain the session counter as an integer or other data object that is incremented for each therapy session of a particular patient. In some examples, processor 52 may download the session counter data to the IMD implanted within the patient and, at a next programming session, retrieve the session counter and increment the session counter. Combined, the device serial number and session counter may allow the correct data to be associated with the correct patient, and to sequence the settings correctly, even if there are time or clock changes in one of the devices. Processor 52 may further store the serial number of the IMD along with the session counter in memory 54, and may download the serial number/session counter data to the IMD. In this manner, programmer 20 may be capable of determining which IMD was used for a particular therapy session, even when an internal clock of an IMD or programmer drifts or otherwise changes.

In the example of FIG. 20, icons 270 include a programmer icon and a pump icon. The programmer icon indicates that data for the corresponding therapy session is stored in memory 54 of programmer 20, and the pump icon indicates that the data for the corresponding therapy session is stored in memory 40 of IMD 12. In other examples, additional icons may represent additional storage locations, e.g., a central data repository, an additional programmer, an additional device, a personal computer, a handheld device such as a PDA or a cellular telephone, or other storage location. In the example of FIG. 20, therapy session nodes 272A, 272B, and 272C each correspond to the programmer icon, and therapy session nodes 272D, 272E, 272F, 272G, and 272H each correspond to the pump icon. In this manner, a user, such as a clinician, may quickly determine a storage location for therapy session information, e.g., a programmer or an implantable fluid delivery device.

Figure 21:
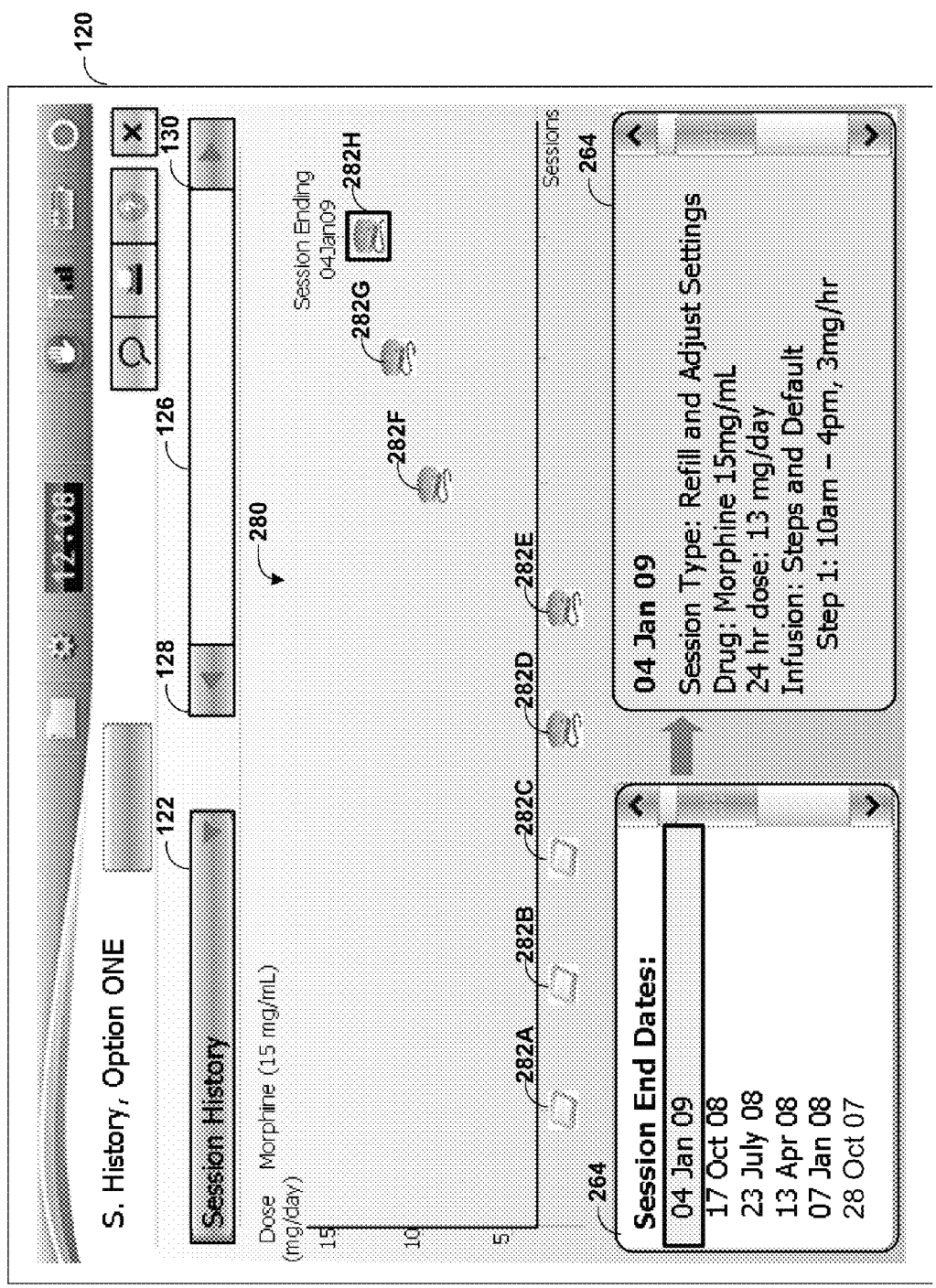
FIG. 21 is a screenshot illustrating another example user interface for displaying a graphical trend of session history information that graphically represents a storage location of the session history information.

FIG. 21 is a screenshot illustrating another example user interface for displaying a graphical trend of session history information that graphically represents a storage location of the session history information. The display in FIG. 21 is similar to that of FIG. 20, except that rather than displaying shapes as the nodes and additional icons, user interface 120 represents nodes 282A-282H (nodes 282) of graph 280 with pump or programmer icons. In the example of FIG. 21, nodes 282A, 282B, and 282C each correspond to the programmer icon, and nodes 282D, 282E, 282F, 282G, and 282H each correspond to the pump icon. FIG. 21 therefore presents an alternative example for representing where data is stored, e.g., either in memory 40 of IMD 12 or in memory 52 of programmer 20. In this example, the programmer or pump icon conveniently indicates where data is stored, but icon shape is not used to present the type of infusion pattern.

Figure 22:
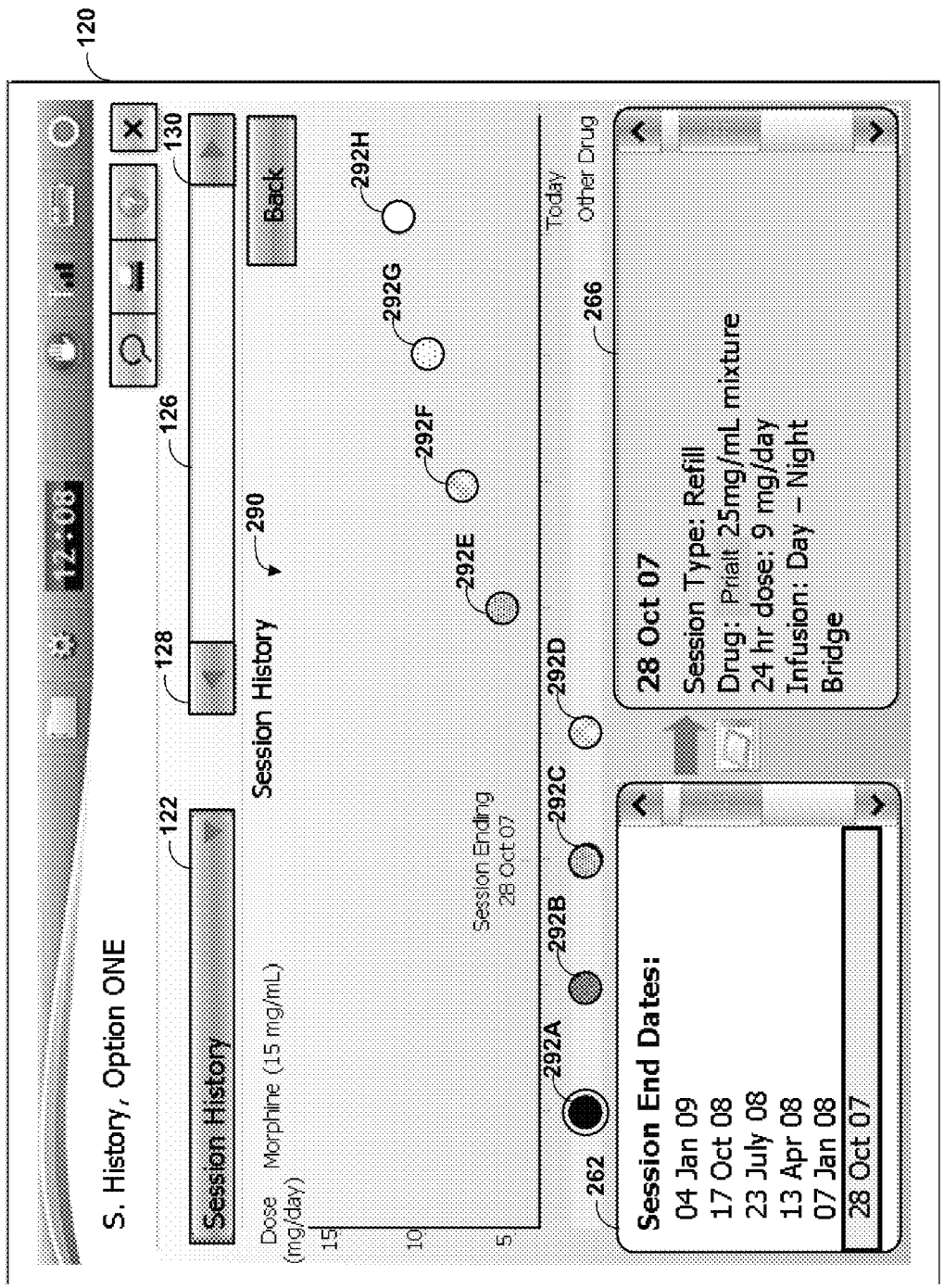
FIG. 22 is a screenshot illustrating an example user interface for displaying a graphical trend of session history information for which nodes represent patient feedback for the corresponding therapy session.

FIG. 22 is a screenshot illustrating an example user interface for displaying a graphical trend of session history information for which nodes represent patient efficacy feedback for the corresponding therapy session. Graph 290 includes nodes 292A-292H (nodes 292) which include similar information to nodes 262 (FIG. 19). In addition, nodes 292 are shaded to represent patient feedback in response to the therapy session. In the example of FIG. 22, darker shading represents negative patient feedback, while lighter shading or no shading represents positive patient feedback.

For example, node 292A has the darkest shading in FIG. 22, indicating that the patient feedback for this session indicated that this session resulted in the worst relative efficacy result, e.g., in terms of symptom relief and/or side effects, whereas node 292H has the lightest shading, indicating that the patient feedback for this session indicated that this session resulted in the best relative result. In other examples, patient feedback may be represented as different colors, shading, hatching, outlining, symbols, highlighting, flashing, varying sizes of nodes 292, or other methods. For example, colors of nodes may indicate patient feedback for a corresponding therapy session, such that relative warmth of the coloring of the node may indicate subjective patient feedback regarding efficacy of the therapy session. For examples, warmer colors such as reds, oranges, and yellows, may indicate that the patient believed a corresponding therapy session was relatively more effective, while cooler colors such as blues, greens, and purples, may indicate that the patient believed a corresponding therapy session was relatively less effective. Alternatively, warmer colors may indicate relatively less effective therapy sessions while cooler colors may indicate relatively more effective therapy sessions, based on the patient's subjective feedback.

In the example of FIG. 22, the user has selected node 292A. To depict this, user interface 292 has highlighted node 292A, as well as "28 Oct. 2007" in text box 262. Session information for the therapy session ending Oct. 28, 2007 is displayed in text box 266, including that the session type was a refill, that the therapeutic agent was Prialt in a 25 mg/mL mixture, that the infusion pattern was a day/night pattern, and that a bridge was performed.

Figure 23:
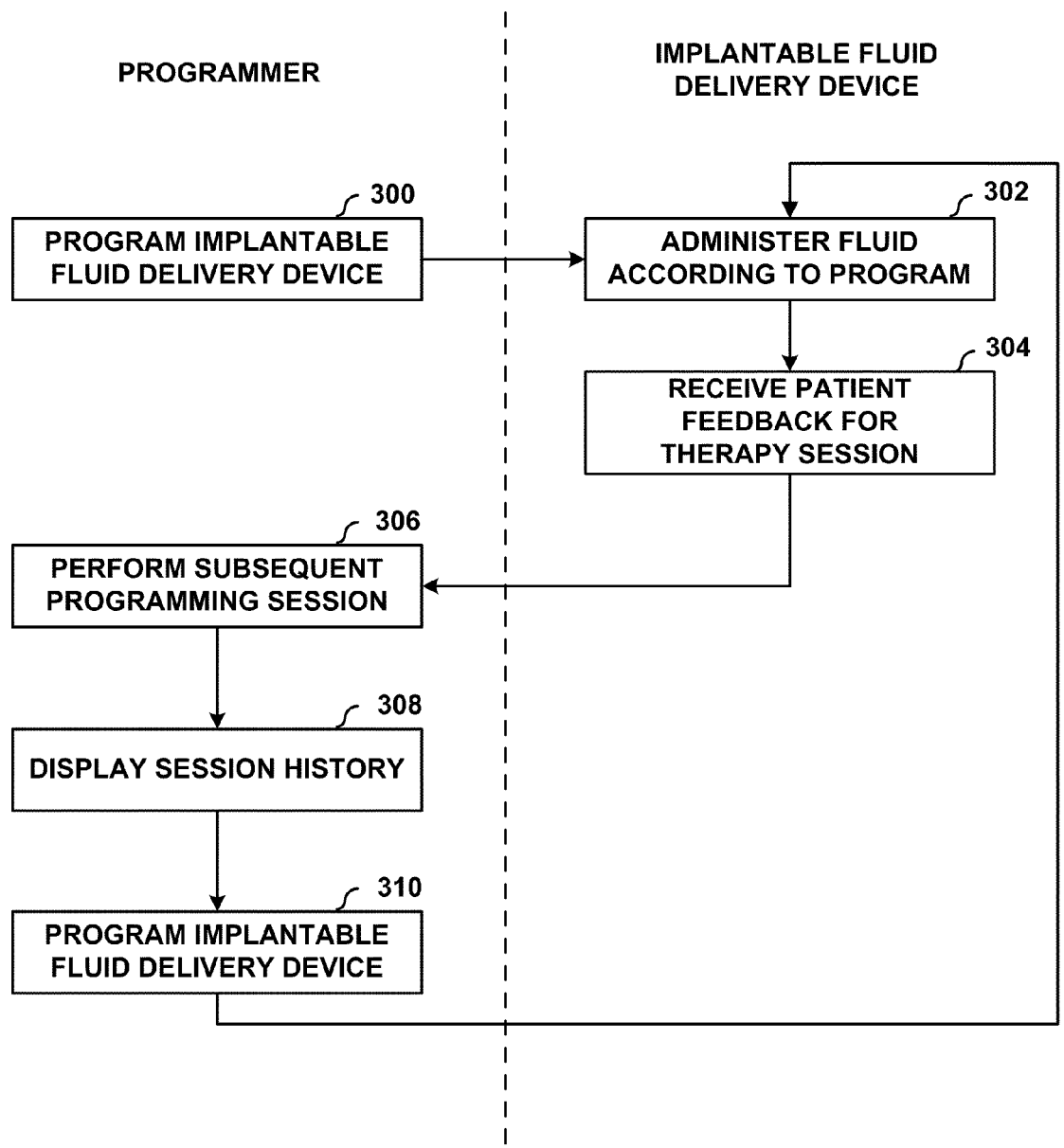
FIG. 23 is a flowchart illustrating an example method for displaying a representation of a plurality of therapy sessions administered by an implantable fluid delivery device to a patient.

FIG. 23 is a flowchart illustrating an example method for displaying a representation of a plurality of therapy sessions administered by an implantable fluid delivery device to a patient. Although discussed with respect to programmer 20 and IMD 12, it should be understood that implantable medical device, and any device for programming the IMD, may implement the example method of FIG. 23.

Initially, a user, such as a clinician, programs IMD 12 using programmer 20 during a programming session to deliver therapy according to a dosing program during a therapy session (300). The therapy session to be administered after the programming session may be referred to as a pending therapy session. The user may program IMD 12 to administer fluid to patient 16 according to various infusion patterns, such as simple continuous, all steps, day/night, or other patterns.

In some examples, the user may program IMD 12 to enable patient-requested supplemental boluses. For example, the user may program IMD 12 to deliver supplemental boluses in response to patient requests, which may include a maximum number of requests. The maximum number of requests may be defined as a number of requests, a maximum amount of extra therapeutic agent, a maximum amount of extra fluid, a percent of the average daily dose, or other measurement.

The user may add clinician annotations to the therapy session. In some examples, when the programming session occurs after an earlier therapy session, the user may also add patient annotations to the earlier therapy session. The user may further define an end date for the pending therapy session, a type of therapeutic agent to be administered, patient data, or other information.

After programming IMD 12, IMD 12 administers fluid containing a therapeutic agent to patient 16 according to the dosing program (302). IMD 12 may also receive information from patient 16 (304), such as, for example, patient efficacy feedback, patient requests for supplemental boluses, or other data, during the therapy session. The therapy session is referred to as a "current" therapy session while IMD 12 is administering the dosing program for the therapy session. The patient feedback may be entered by the patient via the patient programmer, and stored in IMD 12 and/or the patient programmer.

Once the therapy session has ended, patient 16 may return to a clinic or other location to perform a subsequent programming session (306). The recently ended therapy session is referred to then as a "previous" therapy session. During this programming session, a user (who may be the same user as the one who initially programmed IMD 12) may retrieve any data collected by IMD 12 (using programmer 20 or a different programming device), such as patient feedback, patient requests for supplemental boluses, or other patient data. In some cases, the patient feedback may be retrieved from the patient programmer. However, it may be more convenient to permit programmer 20 to retrieve all information from IMD 12. The user may also ask patient 16 for feedback regarding the previous therapy session and enter this information into the programmer as a patient annotation.

The programmer may then display a session history as a representation of earlier therapy sessions, including the previous therapy session, administered by IMD 12 to patient 16 (308). In this manner, the programmer may display a representation of a plurality of therapy sessions that includes at least one therapy session for which information was retrieved from an implantable fluid delivery device. The retrieved information may include the dosing program, infusion pattern, actions taken during a clinical programming session, sensed events or diagnostic detections, patient feedback, clinician annotations, patient requested supplemental boluses, a number of supplemental boluses actually delivered by IMD 12, or any other information regarding the therapy session generated by a programmer device or IMD 12 (or other implantable medical device used to treat patient 16).

Using the displayed information, the user may program IMD 12 according to a new dosing program for a subsequent therapy session (310), and IMD 12 may then administer fluid according to the new program (302). For example, the user may determine whether the infusion pattern(s) for earlier therapy sessions, the average daily dose of therapeutic agent, or other programmed factors resulted in optimal results with minimal side effects. The user may also determine whether to modify infusion patterns for a pending therapy session based on, for example, times of patient requested supplemental boluses. IMD 12 may then administer fluid according to the new programming. In this manner, the user may use the displayed information to determine settings for a pending dosing program.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components.

The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable medium may cause a programmable processor, or other processor, to perform the method, e.g., when the instructions are executed. Computer-readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

The invention claimed is:

1. A method comprising:
retrieving, with a device for programming an implantable fluid delivery device, therapy session information for a plurality of therapy sessions administered by the implantable fluid delivery device to a patient, wherein each of the plurality of therapy sessions occurs between a respective set of two of a plurality of programming sessions during which the implantable fluid delivery device is programmed; and
displaying, with the device, a representation of the plurality of therapy sessions, wherein the representation comprises an abstraction of the therapy session information.

2. The method of claim 1, wherein the representation comprises a graphical representation.

3. The method of claim 2, wherein the graphical representation comprises a plurality of nodes, each of the nodes corresponding to one of the plurality of therapy sessions.

4. The method of claim 3, wherein horizontal positions of the nodes on the graphical representation indicate relative dates on which the corresponding therapy sessions ended.

5. The method of claim 3, wherein vertical positions of the nodes on the graphical representation indicate average daily doses of a therapeutic agent administered by the implantable fluid delivery device during the corresponding therapy sessions.

6. The method of claim 3, wherein shapes of the nodes on the graphical representation indicate infusion patterns according to which the implantable fluid delivery device administered fluid during the corresponding therapy sessions.

7. The method of claim 3, wherein colors of the nodes on the graphical representation indicate patient feedback for the corresponding therapy sessions.

8. The method of claim 3, further comprising:
receiving a user selection of one of the plurality of nodes; and
displaying a textual representation of the therapy session corresponding to the selected node.

9. The method of claim 8, wherein the textual representation comprises a clinician annotation for the corresponding therapy session.

10. The method of claim 8, wherein the textual representation comprises patient feedback for the corresponding therapy session.

11. The method of claim 3, wherein the plurality of nodes comprises a first plurality of nodes, the method further comprising displaying a second plurality of nodes, each of the second plurality of nodes representing patient feedback for a corresponding one of the therapy sessions.

12. The method of claim 1, further comprising displaying an indication that a one-time event occurred for at least one of the plurality of therapy sessions, wherein the one-time event comprises one of a prime, a bridge, a therapeutic bolus, and a catheter length change.

13. The method of claim 1, further comprising displaying a representation of a sensed diagnostic event comprising at least one of a malfunction of a component of the implantable fluid delivery device, a catheter replacement, a catheter length revision, a revision to a dosing program downloaded to the implantable fluid delivery device, a reservoir refill, a reservoir flush, and an accesses to a catheter port.

14. The method of claim 1, wherein retrieving comprises retrieving the therapy session information from a computer-readable medium of the programming device.

15. The method of claim 1, wherein retrieving comprises retrieving the therapy session information from a computer-readable medium of the implantable fluid delivery device.

16. The method of claim 1, further comprising displaying an indication that information for at least one therapy session is missing.

17. The method of claim 1, wherein the representation comprises textual representations for each of the displayed therapy sessions.

18. The method of claim 1, further comprising displaying an indication of a percentage of therapeutic agent administered as a result of patient requests.

19. The method of claim 18, further comprising retrieving from the implantable fluid delivery device data related to the percentage of therapeutic agent.

20. A programmer device comprising:
a user interface comprising a display to present a representation of a plurality of therapy sessions administered by an implantable fluid delivery device to a patient, wherein each of the plurality of therapy sessions occurs between a respective set of two of a plurality of programming sessions during which the implantable fluid delivery device is programmed, and wherein the representation comprises an abstraction of therapy session information for the plurality of therapy sessions; and
a processor that controls the user interface to present on the display the representation of the plurality of therapy sessions.

21. The device of claim 20, wherein the representation comprises a graphical representation.

22. The device of claim 21, wherein the graphical representation comprises a plurality of nodes, each of the nodes corresponding to one of the plurality of therapy sessions.

23. The device of claim 22, wherein horizontal positions of the nodes on the graphical representation indicate relative dates on which the corresponding therapy session ended, and wherein vertical positions of the nodes on the graphical representation indicate average daily doses of a therapeutic agent administered by the implantable fluid delivery device during the corresponding therapy sessions.

24. The device of claim 22, wherein shapes of the nodes on the graphical representation indicate infusion patterns according to which the implantable fluid delivery device administered fluid during the corresponding therapy sessions.

25. The device of claim 22, wherein colors of the nodes on the graphical representation indicate patient feedback for the corresponding therapy sessions.

26. The device of claim 22, further comprising a user interface configured to receive a user selection of one of the plurality of nodes, wherein the processor causes the user interface to display a textual representation of the therapy session corresponding to the selected node.

27. The device of claim 26, wherein the textual representation comprises at least one of a clinician annotation for the corresponding therapy session and patient feedback for the corresponding therapy session.

28. The device of claim 22, wherein the plurality of nodes comprises a first plurality of nodes, the device further comprising displaying a second plurality of nodes, each of the second plurality of nodes representing patient feedback for a corresponding one of the therapy sessions.

29. The device of claim 20, wherein the processor causes the user interface to display an indication that information for at least one therapy session is missing.

30. The device of claim 20, wherein the processor causes the user interface to display an indication of a percentage of therapeutic agent administered as a result of patient requests.

31. A system comprising:
an implantable fluid delivery pump that delivers fluid to a patient according to a selected dosing program, comprising a telemetry module; and
a programmer device comprising:
a telemetry module to send signals to the implantable fluid delivery pump to program the implantable fluid delivery pump;
a user interface comprising a display to present a representation of a plurality of therapy sessions administered by the implantable fluid delivery device to a patient, wherein each of the plurality of therapy sessions occurs between a respective set of two of a plurality of programming sessions during which the implantable fluid delivery device is programmed, and wherein the representation comprises an abstraction of therapy session information for the plurality of therapy sessions; and
a processor that controls the user interface to present on the display the representation of the plurality of therapy sessions.

32. The system of claim 31, wherein the representation comprises a graphical representation comprising plurality of nodes, each of the nodes corresponding to one of the plurality of therapy sessions.

33. The system of claim 32, wherein horizontal positions of the nodes on the graphical representation indicate relative dates on which the corresponding therapy session ended, and wherein vertical positions of the nodes on the graphical representation indicate average daily doses of a therapeutic agent administered by the implantable fluid delivery device during the corresponding therapy sessions.

34. The system of claim 32, wherein the programmer device further comprises a user interface configured to receive a user selection of one of the plurality of nodes, wherein the processor of the programmer device causes the user interface to display a textual representation of the therapy session corresponding to the selected node.

35. A computer-readable medium encoded with instructions for causing a programmable processor of a programmer device for programming an implantable fluid deliver device to:
retrieve therapy session information for a plurality of therapy sessions administered by the implantable fluid delivery device to a patient; and
display a representation of the plurality of therapy sessions, wherein each of the plurality of therapy sessions occurs between a respective set of two of a plurality of programming sessions during which the implantable fluid delivery device is programmed, and wherein the representation comprises an abstraction of the therapy session information.

36. The computer-readable medium of claim 35, wherein the representation comprises a graphical representation, and the graphical representation comprises a plurality of nodes, each of the nodes corresponding to one of the plurality of therapy sessions.

37. The computer-readable medium of claim 36, wherein horizontal positions of the nodes on the graphical representation indicate relative dates on which the corresponding therapy session ended, and wherein vertical positions of the nodes on the graphical representation indicate an average daily dose of a therapeutic agent administered by the implantable fluid delivery device during the corresponding therapy session.

38. The computer-readable medium of claim 37, wherein shapes of the nodes on the graphical representation indicate infusion patterns according to which the implantable fluid delivery device administered fluid during the corresponding therapy sessions.

39. A medical device comprising:
means for retrieving therapy session information for a plurality of therapy sessions administered by an implantable fluid delivery device to a patient; and
means for displaying a representation of the plurality of therapy sessions, wherein each of the plurality of therapy sessions occurs between a respective set of two of a plurality of programming sessions during which the implantable fluid delivery device is programmed, and wherein the representation comprises an abstraction of the therapy session information.

40. The medical device of claim 39, wherein the representation comprises a graphical representation, and the graphical representation comprises a plurality of nodes, each of the nodes corresponding to one of the plurality of therapy sessions.

41. The medical device of claim 40, wherein horizontal positions of the nodes on the graphical representation indicate relative dates on which the corresponding therapy session ended, and wherein vertical positions of the nodes on the graphical representation indicate an average daily dose of a therapeutic agent administered by the implantable fluid delivery device during the corresponding therapy session.

42. The medical device of claim 41, wherein shapes of the nodes on the graphical representation indicate infusion patterns according to which the implantable fluid delivery device administered fluid during the corresponding therapy sessions.

43. The method of claim 1, further comprising programming, by the device during one of the programming sessions, the implantable fluid delivery device to administer fluid to the patient according to a dosing program corresponding to one of the therapy sessions, wherein the dosing program defines one or more therapy schedules, each of the therapy schedules defining a rate at which to administer the fluid and a duration of time over which to administer the fluid at the rate.

44. The method of claim 1, wherein the abstraction of the therapy session information summarizes differences between the therapy sessions.

45. The method of claim 6, wherein the infusion patterns comprise one of:
- a simple continuous pattern;
- a day and night pattern; or
- an all steps flex pattern.

* * * * *